(12) United States Patent
Ito et al.

(10) Patent No.: US 9,851,305 B2
(45) Date of Patent: Dec. 26, 2017

(54) SURFACE-ENHANCED RAMAN SCATTERING UNIT AND RAMAN SPECTROSCOPIC ANALYSIS METHOD

(71) Applicant: HAMAMATSU PHOTONICS K.K., Hamamatsu-shi, Shizuoka (JP)

(72) Inventors: Masashi Ito, Hamamatsu (JP); Katsumi Shibayama, Hamamatsu (JP); Kazuto Ofuji, Hamamatsu (JP); Hiroki Oyama, Hamamatsu (JP); Yoshihiro Maruyama, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 14/780,755

(22) PCT Filed: Feb. 7, 2014

(86) PCT No.: PCT/JP2014/052928
§ 371 (c)(1),
(2) Date: Sep. 28, 2015

(87) PCT Pub. No.: WO2014/156331
PCT Pub. Date: Oct. 2, 2014

(65) Prior Publication Data
US 2016/0054227 A1    Feb. 25, 2016

(30) Foreign Application Priority Data

Mar. 29, 2013  (JP) .................................. 2013-073315

(51) Int. Cl.
*G01N 21/01* (2006.01)
*G01N 21/65* (2006.01)
(Continued)

(52) U.S. Cl.
CPC .............. *G01N 21/658* (2013.01); *B01L 9/52* (2013.01); *G02B 21/34* (2013.01);
(Continued)

(58) Field of Classification Search
CPC ...... G01N 21/658; A61B 8/463; A61B 8/467; A61B 8/5207; A61B 8/5246;
(Continued)

(56) References Cited

U.S. PATENT DOCUMENTS 4,589,551 A   5/1986  Hellon
5,090,568 A   2/1992  Tse
(Continued)

FOREIGN PATENT DOCUMENTS

CN    101281133    10/2008
CN    101319994    12/2008
(Continued)

OTHER PUBLICATIONS

W. Zhang et al., "Giant and uniform fluorescence enhancement over large areas using plamonic nanodots in 3D resonant cavity nanoantenna by nanoimprinting", Nanotechnology, vol. 23, No. 22, May 10, 2012, p. 225301, XP20224099.

(Continued)

*Primary Examiner* — Tri T Ton
(74) *Attorney, Agent, or Firm* — Drinker Biddle & Reath LLP

(57) ABSTRACT

A SERS unit 1A comprises a SERS element 2 having a substrate 21 and an optical function part 20 formed on the substrate 21, the optical function part 20 for generating surface-enhanced Raman scattering; a transportation board 3 supporting the SERS element 2 during transportation, the SERS element 2 being removed from the transportation board 3 upon measurement; and a holding part 4 having a pinching part 41 pinching the SERS element 2 in coopera- (Continued)

tion with the transportation board 3, and detachably holding the SERS element 2 in the transportation board 3.

18 Claims, 23 Drawing Sheets

(51) Int. Cl.
*B01L 9/00* (2006.01)
*G02B 21/34* (2006.01)

(52) U.S. Cl.
CPC ..... *B01L 2200/18* (2013.01); *B01L 2300/041* (2013.01); *B01L 2300/0858* (2013.01)

(58) Field of Classification Search
CPC ............. G01S 15/8904; G01S 15/8915; G01S 15/8963; G01S 7/52038; G01S 7/52074; G01S 7/52085; G01S 7/52093; G01S 7/52095
USPC .......................................... 356/244, 247–256
See application file for complete search history.

(56) References Cited

U.S. PATENT DOCUMENTS

| | | | |
|---|---|---|---|
| 7,483,130 | B2 | 1/2009 | Baumberg et al. |
| 7,864,313 | B2 | 1/2011 | Baumberg et al. |
| 2004/0023046 | A1 | 2/2004 | Schlottig et al. |
| 2008/0094621 | A1 | 4/2008 | Li et al. |
| 2008/0218761 | A1 | 9/2008 | Nishikawa et al. |
| 2011/0027901 | A1 | 2/2011 | Gaster et al. |
| 2011/0116089 | A1 | 5/2011 | Schmidt et al. |
| 2011/0166045 | A1 | 7/2011 | Dhawan et al. |
| 2013/0252275 | A1 | 9/2013 | Tokonami et al. |
| 2014/0043605 | A1 | 2/2014 | Tseng et al. |

FOREIGN PATENT DOCUMENTS

| | | |
|---|---|---|
| CN | 101680900 A | 3/2010 |
| CN | 102016585 A | 4/2011 |
| CN | 102282094 | 12/2011 |
| CN | 102483354 | 5/2012 |
| JP | H05/044867 U | 6/1993 |
| JP | 2003-026232 A | 1/2003 |
| JP | 2008-519254 | 6/2008 |
| JP | 2008-196992 | 8/2008 |
| JP | 2009-103643 A | 5/2009 |
| JP | 2009-222507 A | 10/2009 |
| JP | 2009-236830 | 10/2009 |
| JP | 2011-021085 | 2/2011 |
| JP | 2011-033518 A | 2/2011 |
| JP | 2011-075348 A | 4/2011 |
| JP | 2011-107032 A | 6/2011 |
| TW | 200728706 A | 8/2007 |
| TW | 200932913 A | 8/2009 |
| TW | 201111771 A | 4/2011 |
| WO | WO 2006/138442 | 12/2006 |
| WO | WO-2007/149120 A2 | 12/2007 |
| WO | WO 2010/033267 | 3/2010 |
| WO | WO-2012/024006 A2 | 2/2012 |
| WO | WO 2012/077756 | 6/2012 |
| WO | WO 2013/015810 | 1/2013 |
| WO | WO-2014/025033 A1 | 2/2014 |
| WO | WO-2014/025034 A1 | 2/2014 |

OTHER PUBLICATIONS

S. M. Wells et al., "Efficient disc on pillar substrates for surface enhanced Ramam spectroscopy", Chemical Communications—Chemcom, vol. 47, No. 13, Jan. 1, 2011, p. 3814-p. 3816, XP055289549.
U.S. Office Action dated Oct. 14, 2016 that issued in U.S. Appl. No. 14/420,510 including Double Patenting Rejections on pp. 2-14.
English Machine Translation of JP 2011-107032, Nishikawa et al., Jun. 2, 2011 as attached to U.S. Office Action dated Oct. 14, 2016 in U.S. Appl. No. 14/420,510.
Online, Internet, "Q-SERS™ G1 Substrate, URL:http://www.optoscience.com/maker/nanova/Pdf/Q-SERS_G1.pdf," Opto Science, Inc., retrieved on Mar. 21, 2013.
K. Nakamoto et al., "Arrays of Metallic Nanopillars in Holes for Plasmonic Devices", Retrieved from the Internet: URL: http://www.rse.org/images/LOC/2011/PDFs/Papers/596_0021.pdf, Oct. 6, 2011, XP055289892.
M. Tomohiko et al., "New localized surface plasmon resonance sensor utilizing nanoimprinting technology", NSTI Nanotechnology Conference and Trade Show—NSTI Nanotech, vol. 1, May 11, 2006, p. 58-p. 61, XP009098538.
W. D. Li et al.. "Three-dimensional cavity nanoantenna coupled plasmonic nanodots for ultrahigh and uniform surface-enhanced Raman scattering over large area", Optics Express, vol. 19, No. 5, Feb. 14, 2011, p. 3925-3936, XP002751299.
Office Action dated Jan. 20, 2017 in U.S. Appl. No. 14/420,502.

Fig.8
(a)
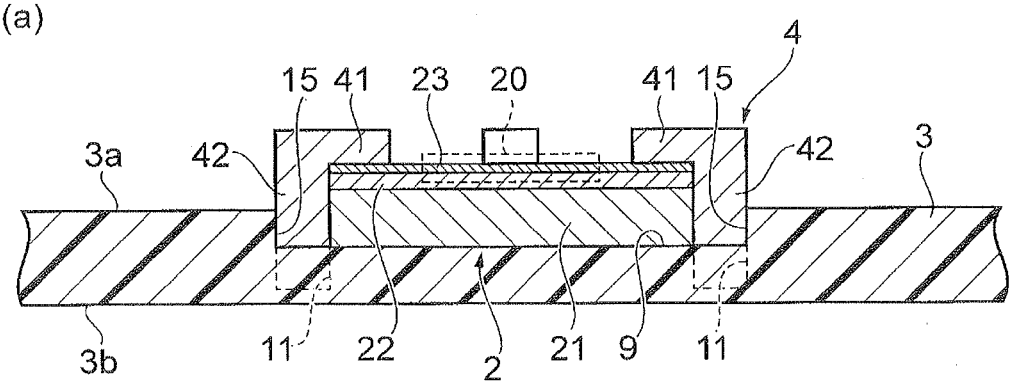
(b)
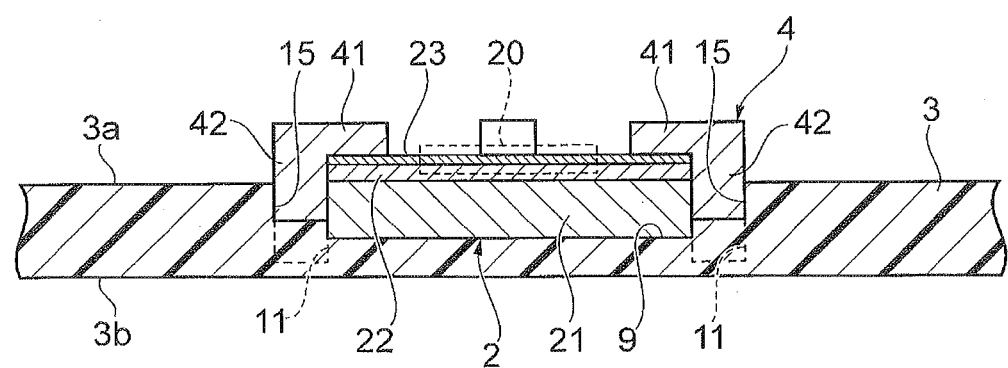

*Fig.10*
(a)
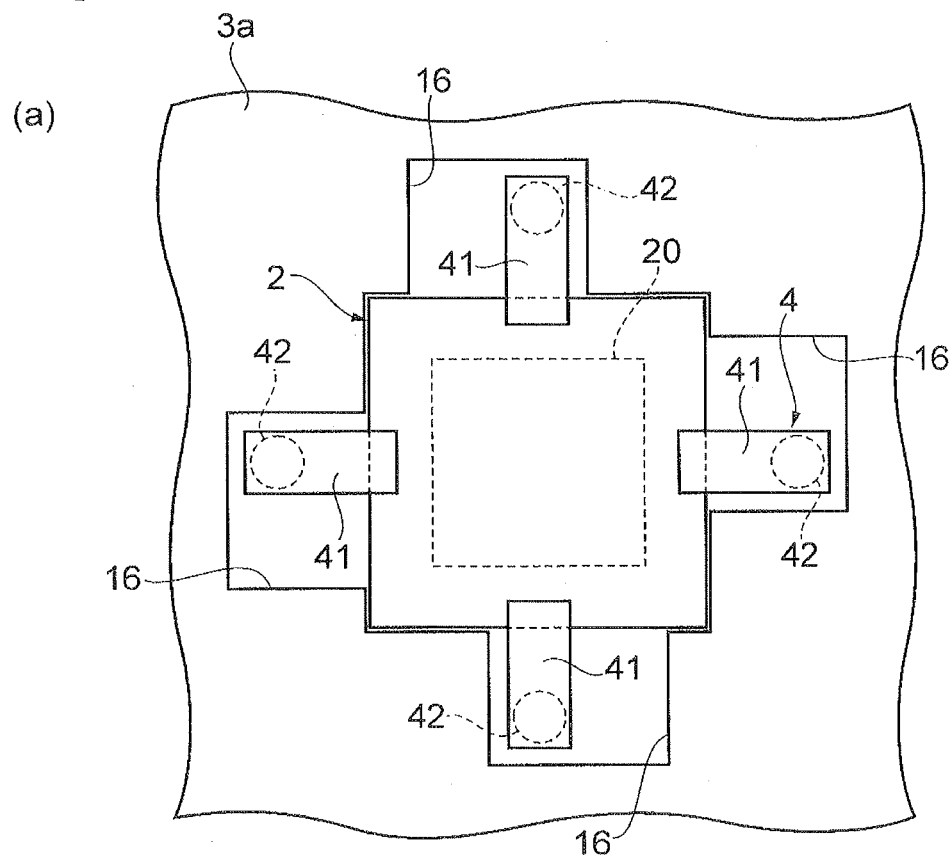
(b)
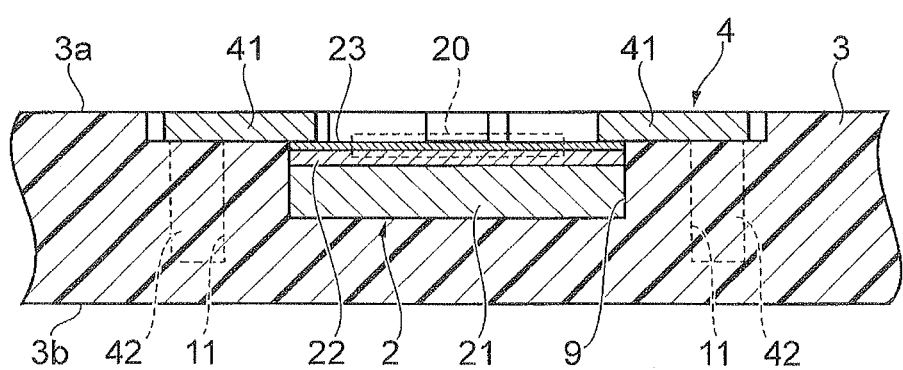

Fig.11
(a)
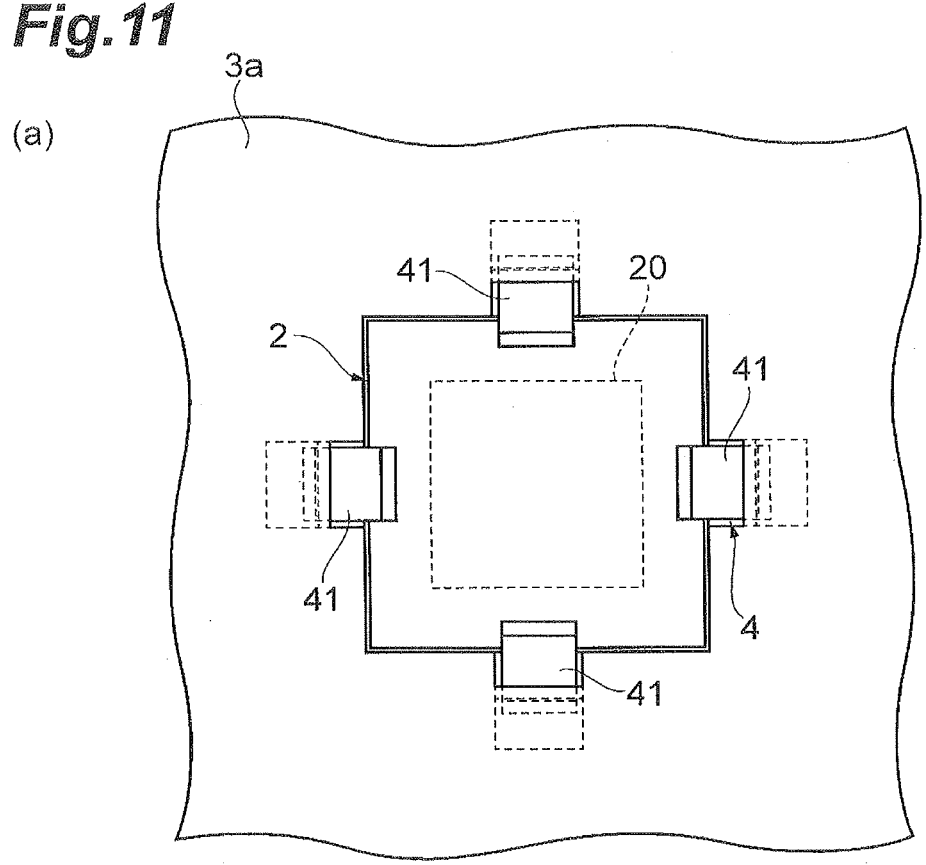
(b)
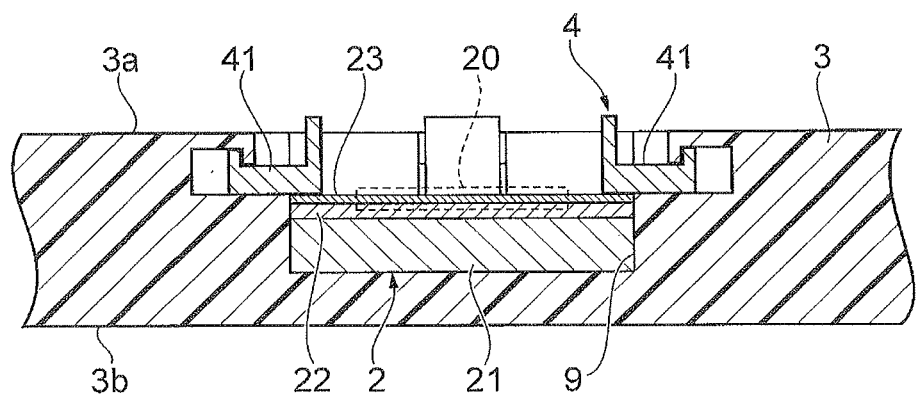

Fig.15
(a) 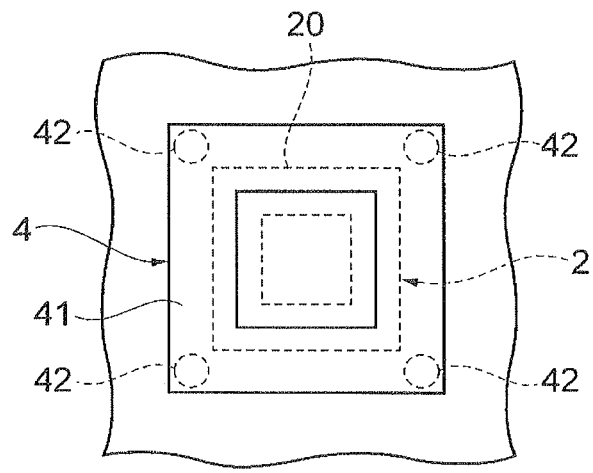
(b) 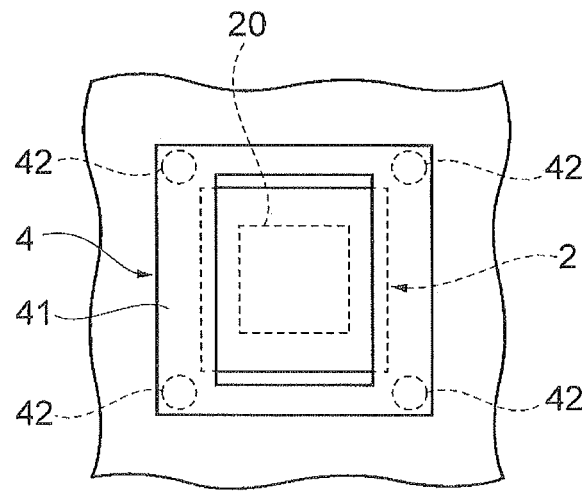
(c) 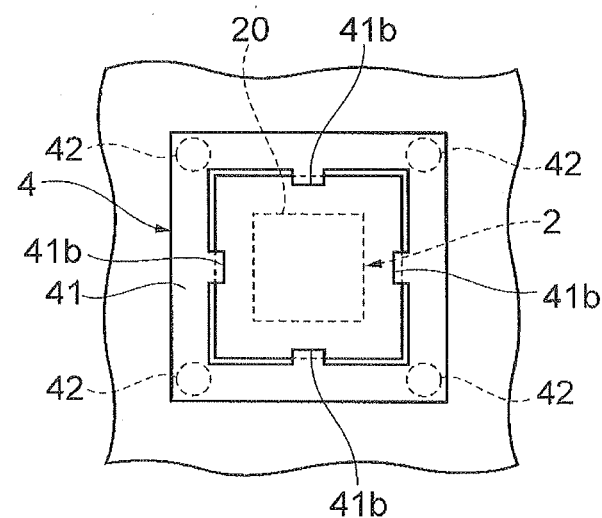

*Fig.16*
(a)
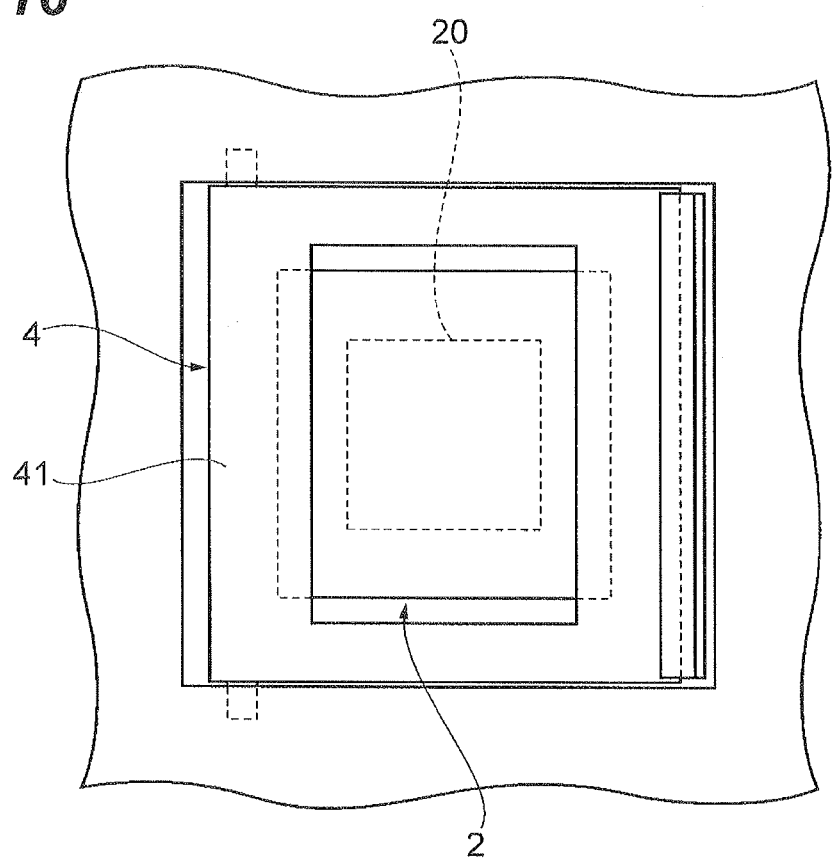
(b)
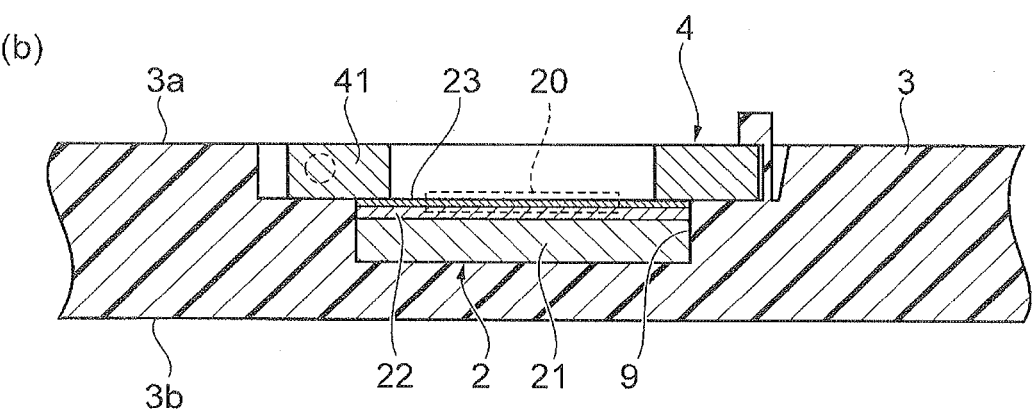

Fig.18
(a)
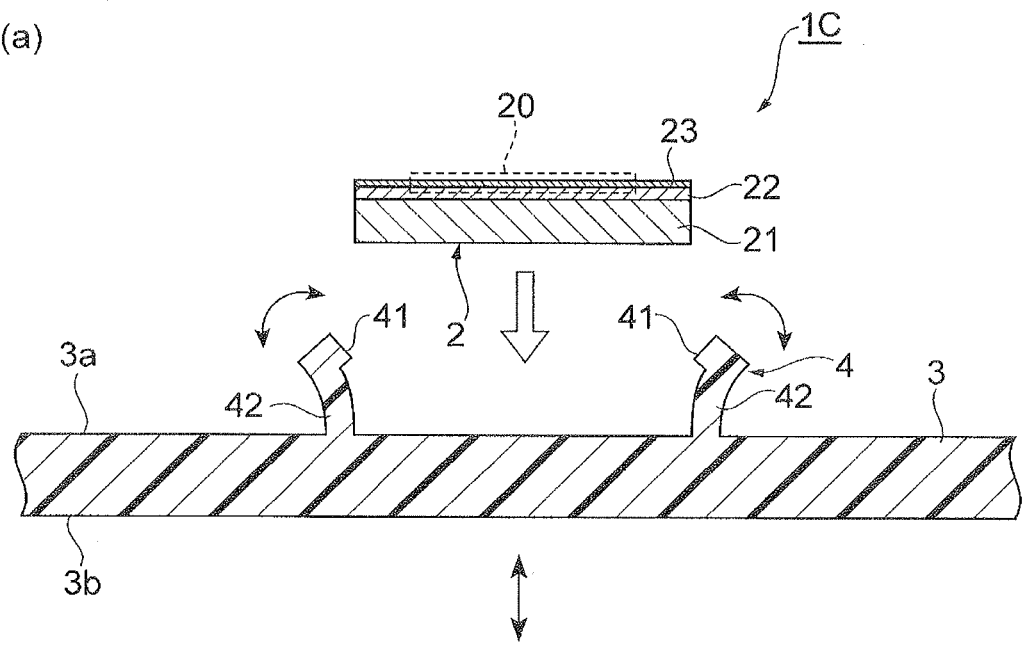
(b)
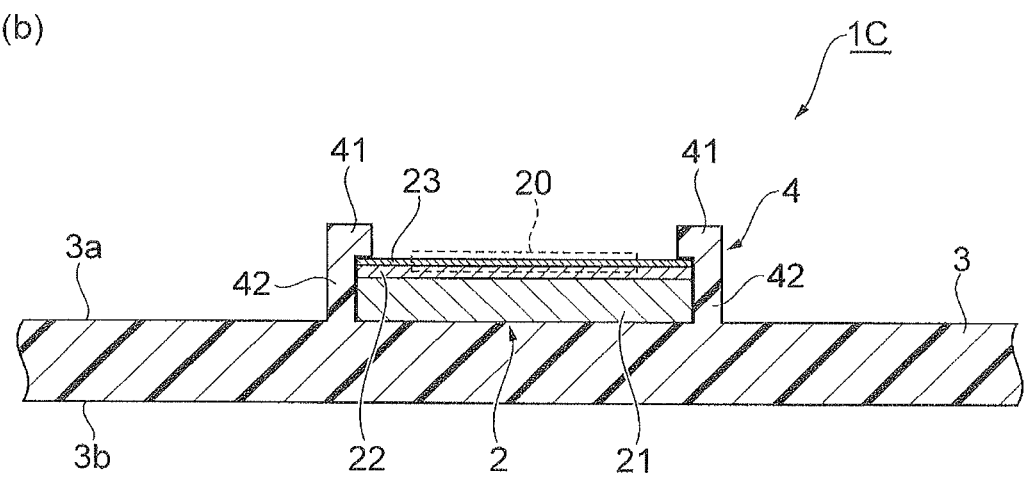

Fig.20
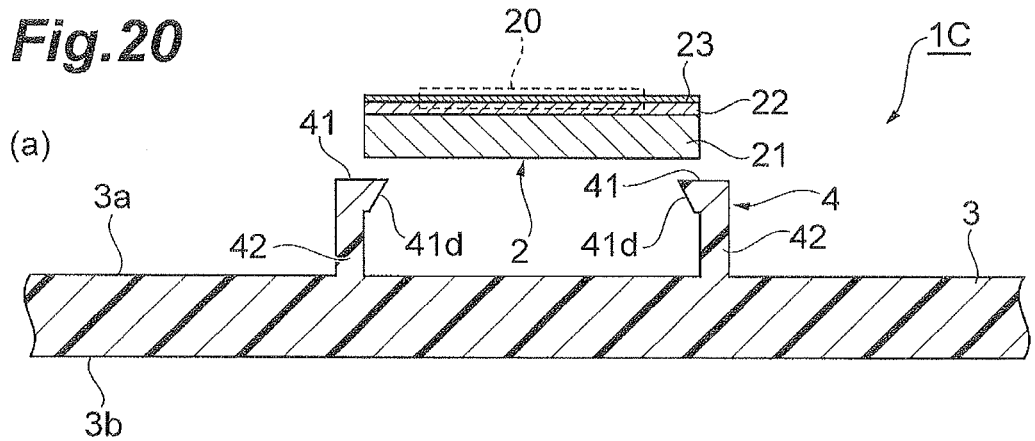
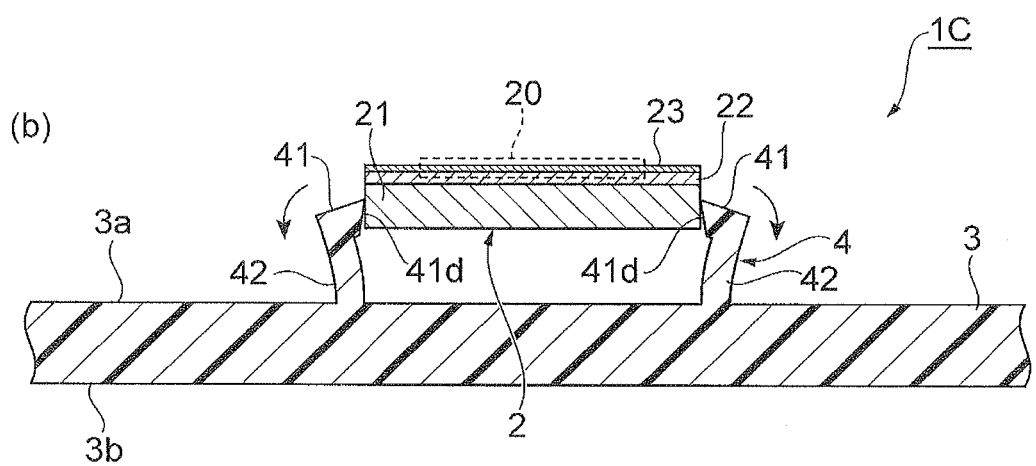
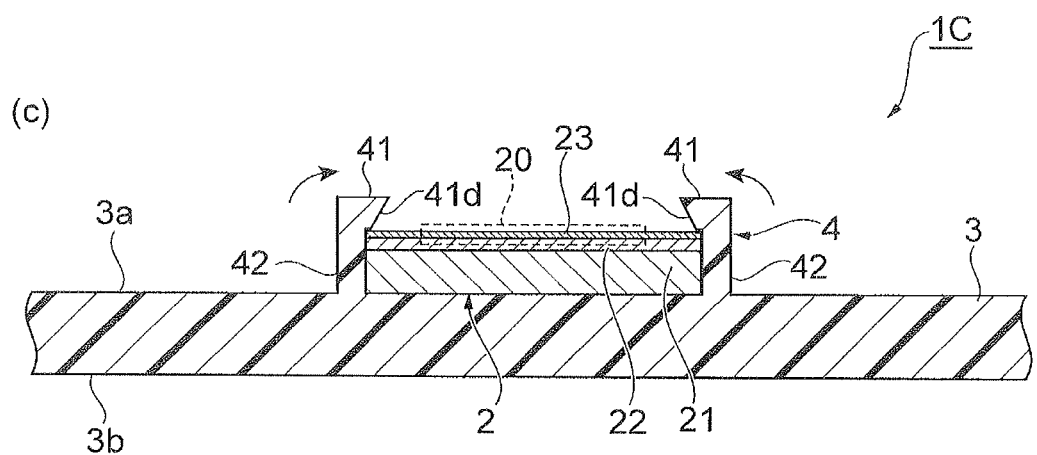

*Fig.21*
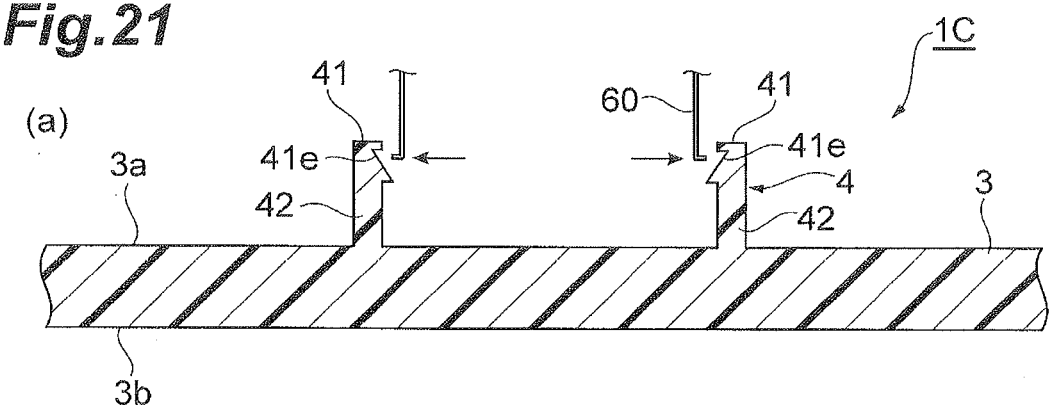
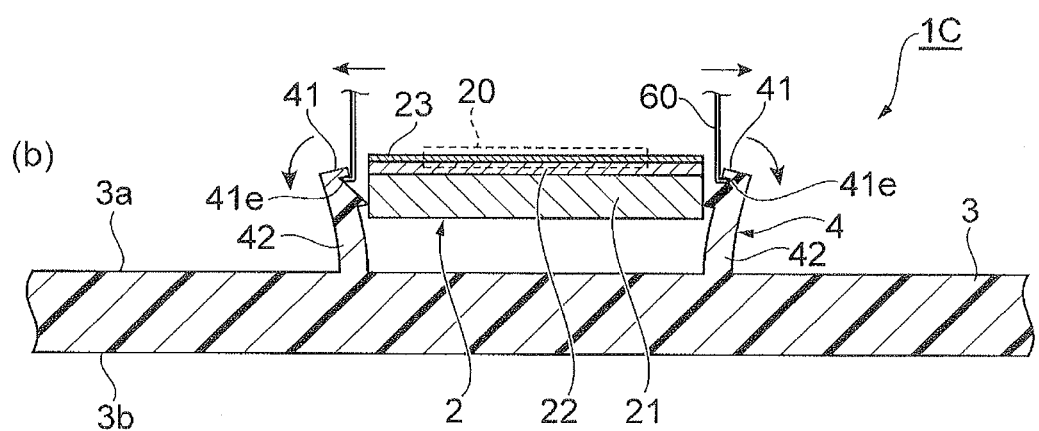
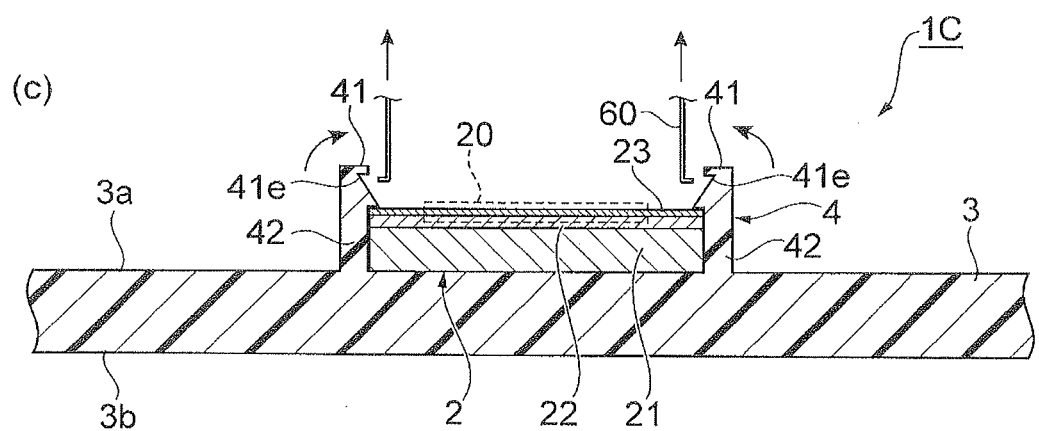

Fig.22
(a)
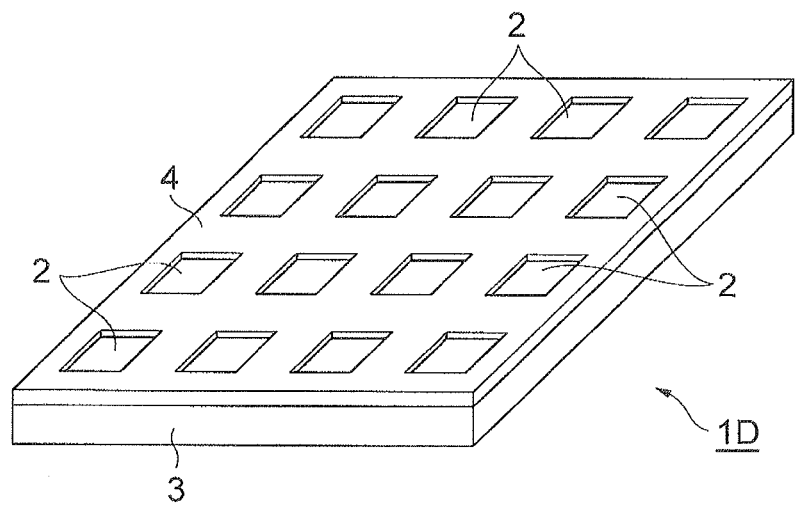
(b)
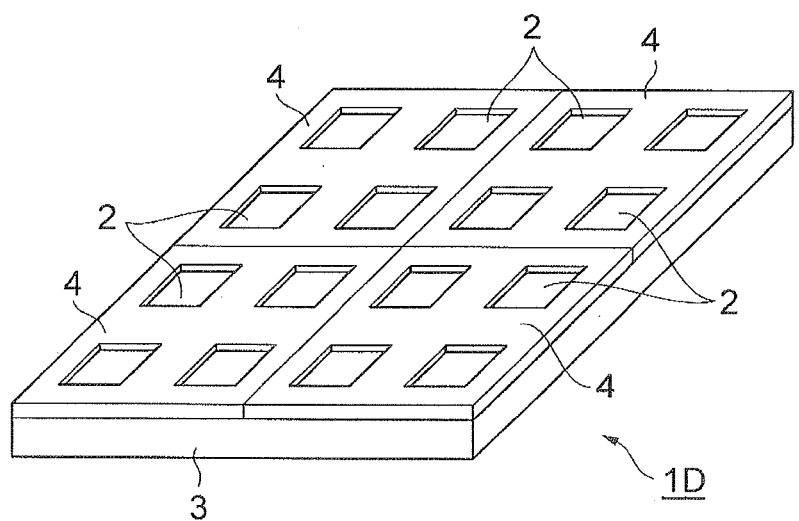
(c)
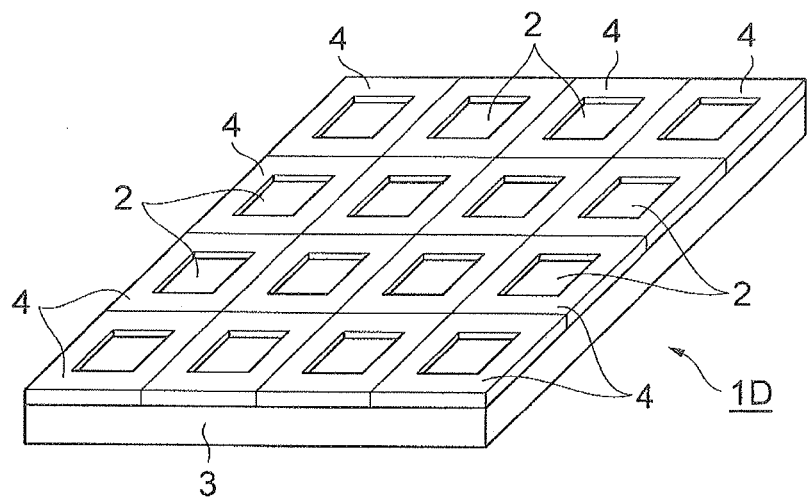

Fig. 23
(a)
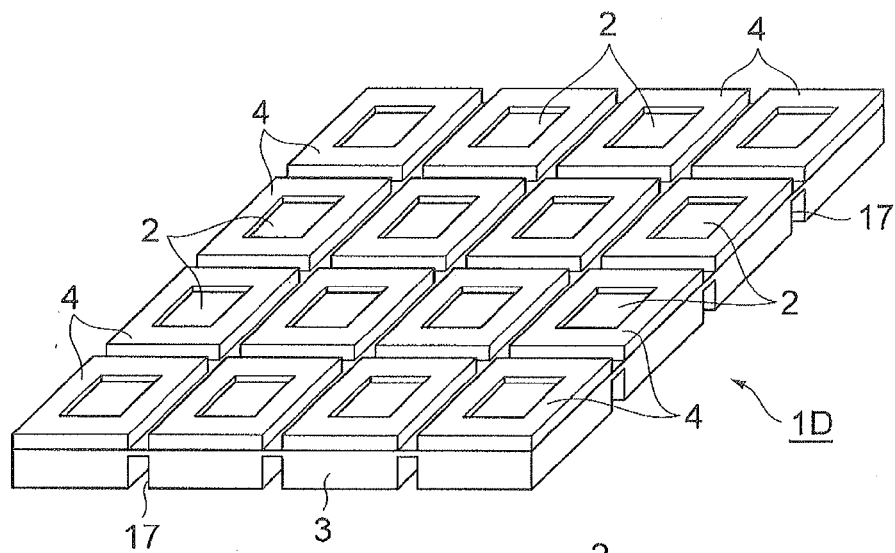
(b)
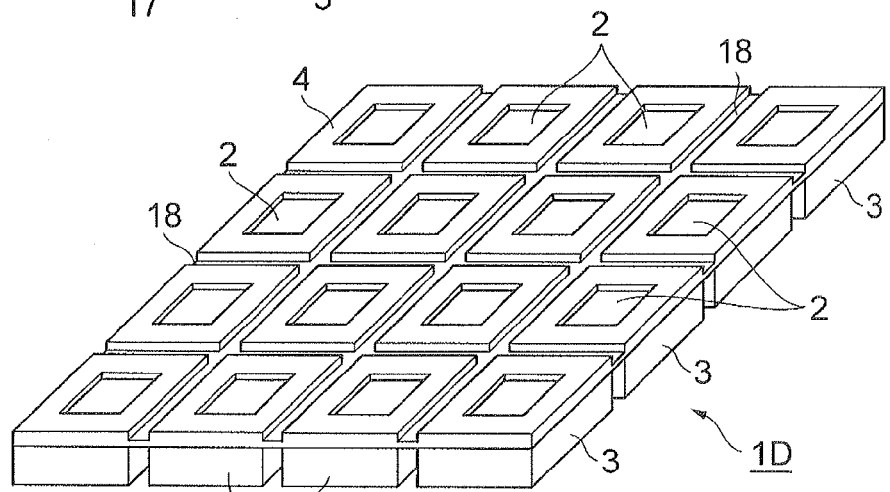
(c)
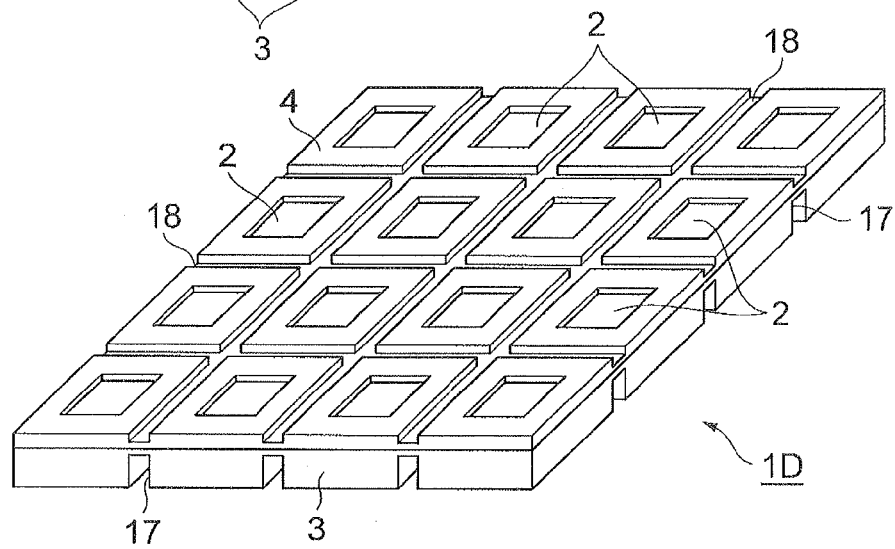

SURFACE-ENHANCED RAMAN SCATTERING UNIT AND RAMAN SPECTROSCOPIC ANALYSIS METHOD

TECHNICAL FIELD

The present invention relates to a surface-enhanced Raman scattering unit and a Raman spectroscopic analysis method.

BACKGROUND ART

Known as a conventional surface-enhanced Raman scattering unit is one in which a surface-enhanced Raman scattering element having an optical function part for generating surface-enhanced Raman scattering (SERS) is secured onto a glass slide (see, for example, Non Patent Literature 1).

CITATION LIST

Non Patent Literature

Non Patent Literature 1: "Q-SERS™ G1 Substrate", [online], Opto Science, Inc., [retrieved on 2013 Mar. 21]. Retrieved from the Internet: <URL: http://www.optoscience.com/maker/nanova/pdf/Q-SERS_G1.pdf>.

SUMMARY OF INVENTION

Technical Problem

While a surface-enhanced Raman scattering unit such as the one mentioned above is set to a Raman spectroscopic analyzer in a unit state (i.e., a state where the surface-enhanced Raman scattering element is secured onto the glass slide), the surface-enhanced Raman scattering element prepared alone may be set to the Raman spectroscopic analyzer as being arranged on a substrate prepared separately or as it is. In such a case, it is necessary for the surface-enhanced Raman scattering element to be transported alone. When the surface-enhanced Raman scattering element is transported while sticking to a gel pack, a tape, or the like in order to prevent it from being damaged, however, the optical function part may deteriorate because of components contained in the gel pack, ingredients of the bonding part of the tape, or the like. When transported as being mounted on an IC chip tray with a cover tray put thereon, on the other hand, the surface-enhanced Raman scattering element may be chipped or damaged because of vibrations during transportation and the like.

It is therefore an object of the present invention to provide a surface-enhanced Raman scattering unit which can inhibit the surface-enhanced Raman scattering element from being damaged and the optical function part from deteriorating during transportation and a Raman spectroscopic analysis method using such a surface-enhanced Raman scattering unit.

Solution to Problem

The surface-enhanced Raman scattering unit in accordance with one aspect of the present invention comprises a surface-enhanced Raman scattering element having a substrate and an optical function part formed on the substrate, the optical function part for generating surface-enhanced Raman scattering; a transportation board supporting the surface-enhanced Raman scattering element during transportation, the surface-enhanced Raman scattering element being removed from the transportation board upon measurement; and a holding part having a pinching part pinching the surface-enhanced Raman scattering element in cooperation with the transportation board, and detachably holding the surface-enhanced Raman scattering element in the transportation board.

In this surface-enhanced Raman scattering unit, the holding part detachably holds the surface-enhanced Raman scattering element in the transportation board. If the surface-enhanced Raman scattering element is transported while sticking to a gel pack, a tape, or the like, deterioration will progress in the optical function part during transportation because of components contained in the gel pack, ingredients of the sticking part of the tape, or the like. However, this surface-enhanced Raman scattering unit does not use tackifiers and/or adhesives of gel packs or tapes and thus can inhibit the optical function part from deteriorating. In addition, the surface-enhanced Raman scattering element is pinched between the transportation board and pinching part. This can hold the surface-enhanced Raman scattering element securely in the transportation board. Therefore, this surface-enhanced Raman scattering unit can inhibit the surface-enhanced Raman scattering element from being damaged and the optical function part from deteriorating during transportation.

In the surface-enhanced Raman scattering unit in accordance with one aspect of the present invention, the holding part may be formed separately from the transportation board and mechanically secured to the transportation board. This configuration can simplify the structure of the transportation board. In addition, as compared with the case where the holding part is secured to the transportation board with a tackifier or adhesive, for example, the optical function part can be inhibited from deteriorating because of ingredients contained in the tackifier or adhesive.

In the surface-enhanced Raman scattering unit in accordance with one aspect of the present invention, the holding part may be formed integrally with the transportation board. This configuration can reduce the number of components in the surface-enhanced Raman scattering unit. In addition, as compared with the case where the holding part is secured to the transportation board with a tackifier or adhesive, for example, the optical function part can be inhibited from deteriorating because of ingredients contained in the tackifier or adhesive.

In the surface-enhanced Raman scattering unit in accordance with one aspect of the present invention, the pinching part may be formed into a ring so as to surround the optical function part when seen in a thickness direction of the substrate, or a plurality of pinching parts may be arranged around the optical function part. These configurations can stably hold the surface-enhanced Raman scattering element in the transportation board.

In the surface-enhanced Raman scattering unit in accordance with one aspect of the present invention, the transportation board may be provided with a depression containing at least a part of the surface-enhanced Raman scattering element on the substrate side and restraining the surface-enhanced Raman scattering element from moving in a direction perpendicular to the thickness direction of the substrate. This configuration can position the surface-enhanced Raman scattering element with respect to the transportation board. This can also more securely prevent the surface-enhanced Raman scattering element from shifting from the transportation board and being damaged during transportation.

In the surface-enhanced Raman scattering unit in accordance with one aspect of the present invention, the transportation board may be formed integrally from a resin. This configuration makes it harder for chipping to occur and thus can more securely inhibit the optical function part from deteriorating because of chipped pieces adhering thereto.

A Raman spectroscopic analysis method in accordance with one aspect of the present invention comprises a first step of preparing the above-mentioned surface-enhanced Raman scattering unit and removing the surface-enhanced Raman scattering element from the transportation board; a second step, after the first step, of arranging a sample on the optical function part of the surface-enhanced Raman scattering element; and a third step, after the second step, of setting the surface-enhanced Raman scattering element to a Raman spectroscopic analyzer, irradiating the sample arranged on the optical function part with excitation light, and detecting Raman-scattered light derived from the sample, so as to perform Raman spectroscopic analysis.

This Raman spectroscopic analysis method uses the surface-enhanced Raman scattering element transported as the above-mentioned surface-enhanced Raman scattering unit and thus can perform the Raman spectroscopic analysis accurately.

Advantageous Effects of Invention

The present invention can provide a surface-enhanced Raman scattering unit which can inhibit the surface-enhanced Raman scattering element from being damaged and the optical function part from deteriorating during transportation and a Raman spectroscopic analysis method using such a surface-enhanced Raman scattering unit.

BRIEF DESCRIPTION OF DRAWINGS

FIG. 8 is a partly enlarged sectional view of a modified example of the surface-enhanced Raman scattering unit of FIG. 1;

FIG. 10 is a set of partly enlarged plan and sectional views of a modified example of the surface-enhanced Raman scattering unit of FIG. 1;

FIG. 11 is a set of partly enlarged plan and sectional views of a modified example of the surface-enhanced Raman scattering unit of FIG. 1;

FIG. 15 is a partly enlarged plan view of modified examples of the surface-enhanced Raman scattering unit of FIG. 13;

FIG. 16 is a set of partly enlarged plan and sectional views of a modified example of the surface-enhanced Raman scattering unit of FIG. 13;

FIG. 18 is a partly enlarged sectional view of the surface-enhanced Raman scattering unit in accordance with a third embodiment of the present invention;

FIG. 20 is a partly enlarged sectional view of a modified example of the surface-enhanced Raman scattering unit of FIG. 18;

FIG. 21 is a partly enlarged sectional view of a modified example of the surface-enhanced Raman scattering unit of FIG. 18;

FIG. 22 is a perspective view of surface-enhanced Raman scattering units in accordance with other embodiments of the present invention; and FIG. 23 is a perspective view of surface-enhanced Raman scattering units in accordance with still other embodiments of the present invention.

DESCRIPTION OF EMBODIMENTS

Figure 1:
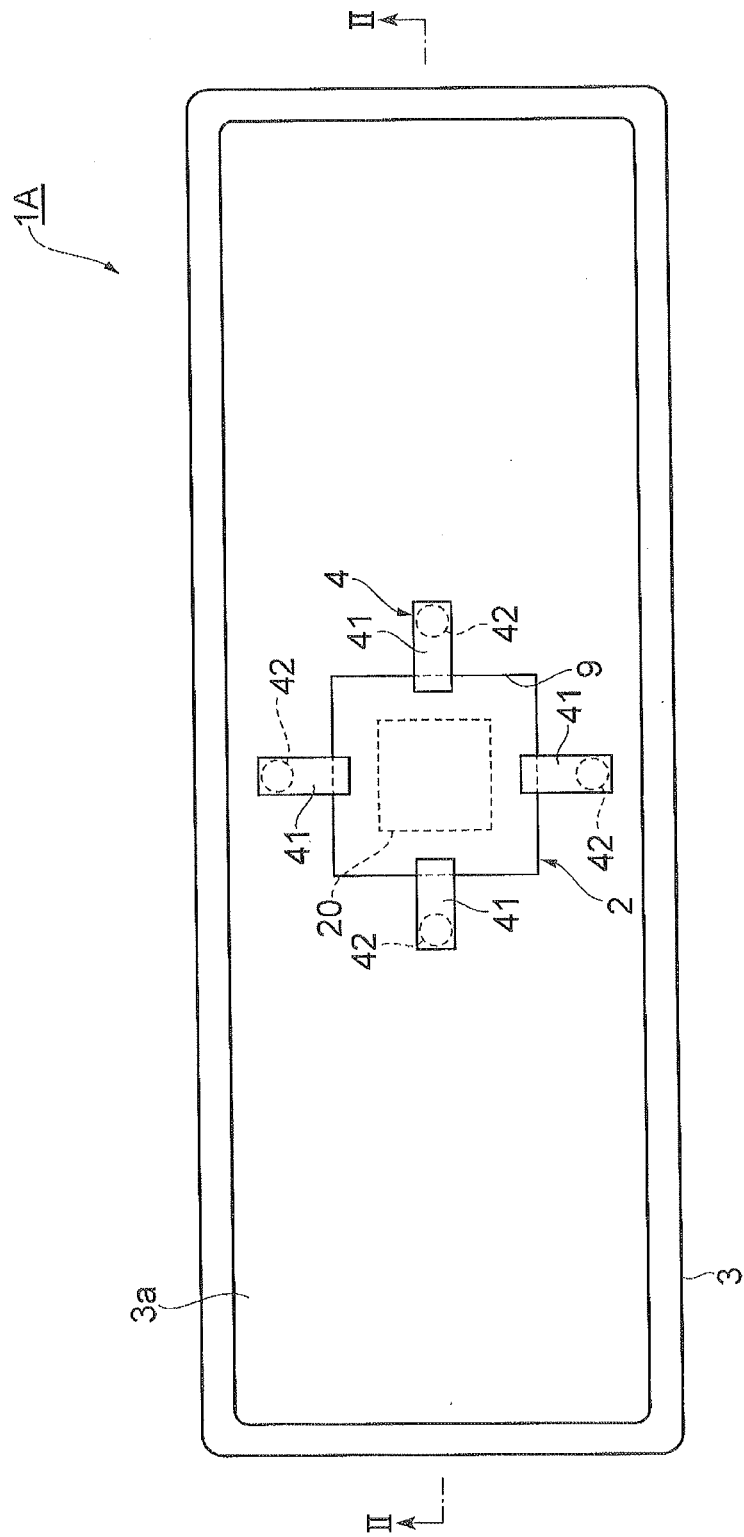
FIG. 1 is a plan view of the surface-enhanced Raman scattering unit in accordance with a first embodiment of the present invention.

In the following, preferred embodiments of the present invention will be explained in detail with reference to the drawings. In the drawings, the same or equivalent constituents will be referred to with the same signs while omitting their overlapping descriptions.

First Embodiment

Figure 2:
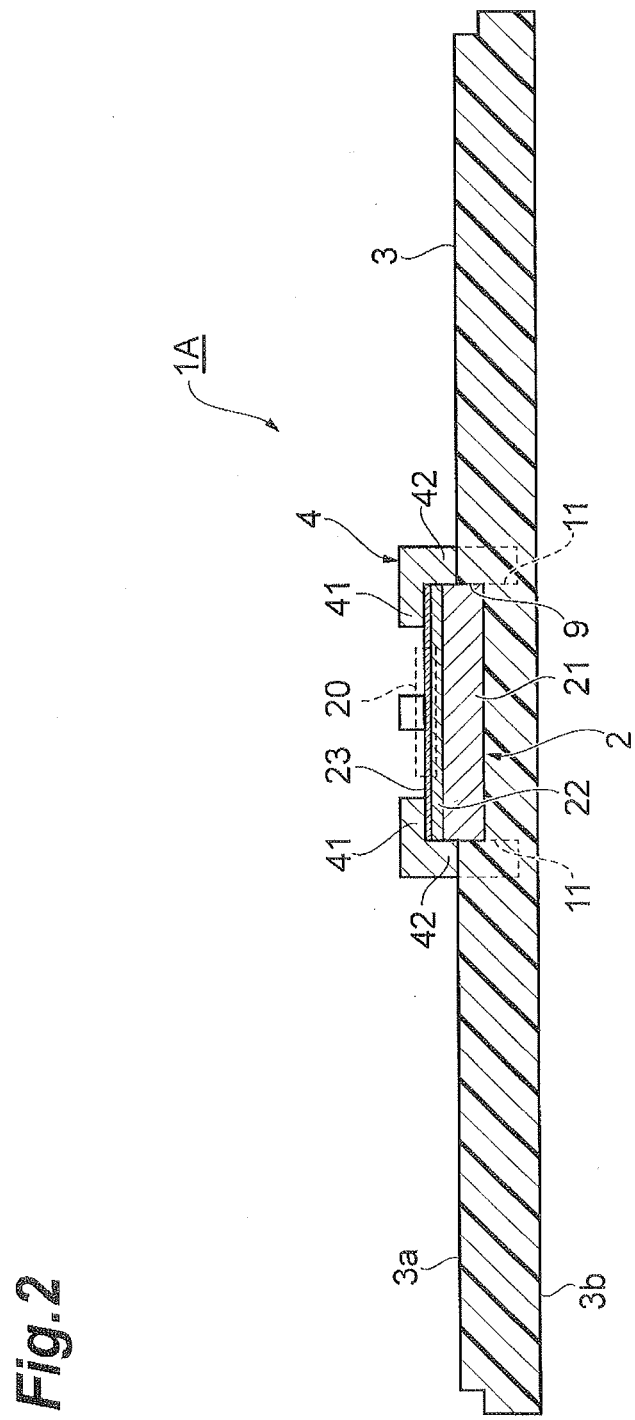
FIG. 2 is a sectional view of the surface-enhanced Raman scattering unit taken along the line of FIG. 1.

As illustrated in FIGS. 1 and 2, a SERS unit (surface-enhanced Raman scattering unit) 1A comprises a SERS element (surface-enhanced Raman scattering element) 2, a transportation board 3 supporting the SERS element 2, and a holding part 4 detachably holding the SERS element 2 in the transportation board 3. The transportation board 3 supports the SERS element 2 during transportation, and the SERS element 2 is removed from the transportation board 3 upon measurement.

The transportation board 3 has a front face 3a provided with a depression 9 containing a part of the SERS element 2 on a substrate 21 side. The depression 9 is formed complementary to a part of the SERS element 2 on the substrate 21 side and restrains the SERS element 2 from moving in directions perpendicular to the thickness direction of the substrate 21. The SERS element 2 is not secured to the inner surface of the depression 9 with an adhesive or the like, but is only in contact with the inner surface of the depression 9. For example, the transportation board 3 is formed into a rectangular plate. The depression 9 is formed into a rectangular parallelepiped. The transportation board 3 is integrally formed from materials such as resins (polypropylene, styrol resin, ABS resin, polyethylene, PET, PMMA, silicone, liquid crystal polymer, etc.), ceramics, glass, and silicon by using techniques such as molding, cutting, and etching.

Figure 3:
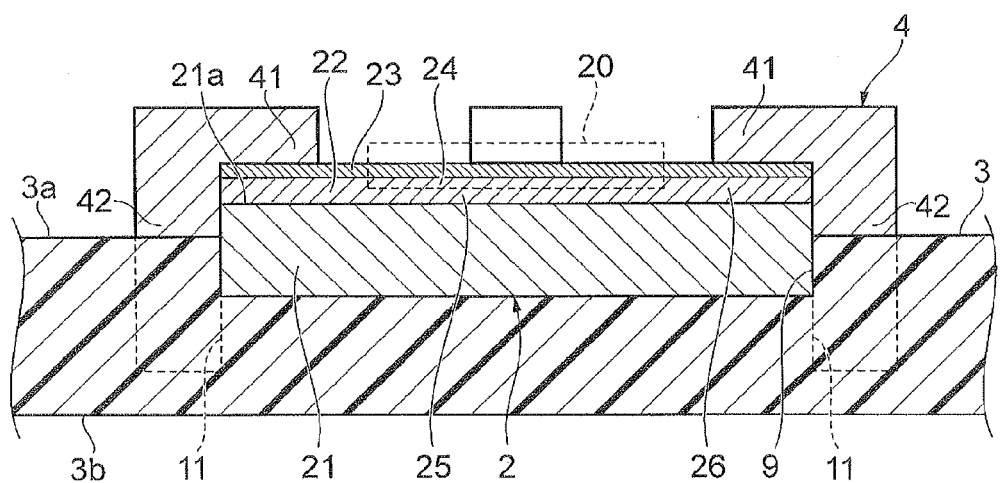
FIG. 3 is a partly enlarged sectional view of the surface-enhanced Raman scattering unit taken along the line II-II of FIG. 1.

As illustrated in FIG. 3, the SERS element 2 comprises a substrate 21, a molded layer 22 formed on the substrate 21, and a conductor layer 23 formed on the molded layer 22. For example, the substrate 21 is formed from silicon, glass, or the like into a rectangular plate having an outer form on the order of several hundred μm×several hundred μm to several ten mm×several ten mm and a thickness on the order of 100 μm to 2 mm.

The molded layer 22 has a fine structure part 24, a support part 25, and a frame part 26. The fine structure part 24, which is a region having a periodic pattern, is formed on a surface layer opposite from the substrate 21 at a center part of the molded layer 22. As the periodic pattern, a plurality of pillars each having a thickness and height on the order of several nm to several hundred nm are periodically arranged at a pitch on the order of several ten nm to several hundred nm in the fine structure part 24. The support part 25, which is a region supporting the fine structure part 24, is formed on a front face 21*a* of the substrate 21. The frame part 26, which is a ring-shaped region surrounding the support part 25, is formed on the front face 21*a* of the substrate 21.

For example, the fine structure part 24 has a rectangular outer form on the order of several hundred μm×several hundred μm to several ten mm×several ten mm when seen from one side in the thickness direction of the transportation board 3. The support part 25 and frame part 26 have a thickness on the order of several ten μm to several ten μm. The molded layer 22 is integrally formed by molding a resin (examples of which include resins based on acrylics, fluorine, epoxy, silicone, and urethane, PET, polycarbonate, and inorganic/organic hybrid materials) or low-melting glass arranged on the substrate 21 by nanoimprinting, for example.

The conductor layer 23 is formed over the fine structure part 24 to the frame part 26. In the fine structure part 24, the conductor layer 23 reaches a surface of the support part 25, exposed to the side opposite from the substrate 21. For example, the conductor layer 23 has a thickness on the order of several urn to several μm. The conductor layer 23 is formed by vapor-depositing a conductor such as a metal (Au, Ag, Al, Cu, Pt, or the like) on the molded layer 22 molded by nanoimprinting, for example.

Figure 4:
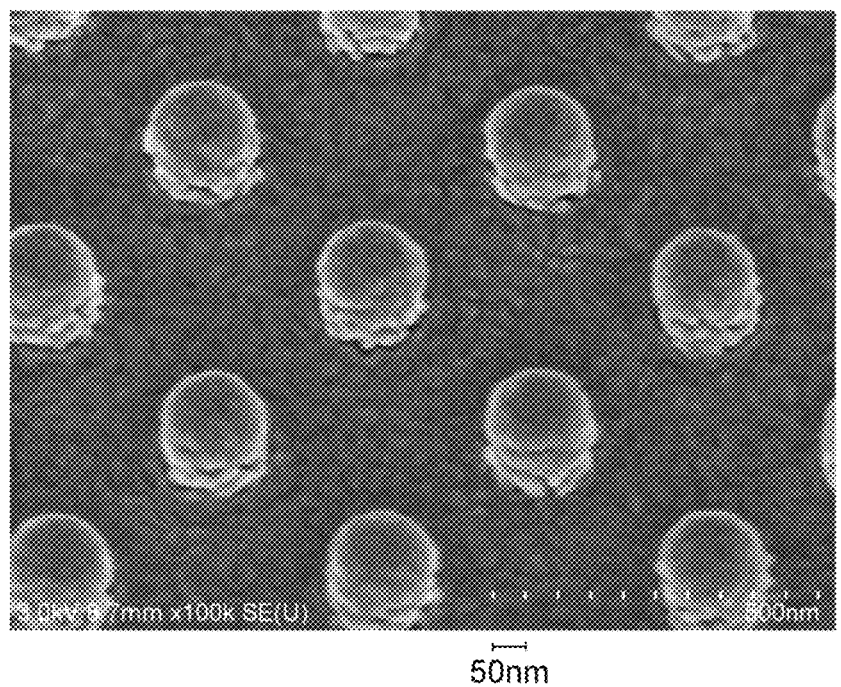
FIG. 4 is a SEM photograph of an optical function part in the surface-enhanced Raman scattering unit of FIG. 1.

In the SERS element 2, the conductor layer 23 formed over the surface of the fine structure part 24 and the surface of the support part 25 exposed to the side opposite from the substrate 21 produces an optical function part 20, which generates surface-enhanced Raman scattering, on the substrate 21. For reference, a SEM photograph of the optical function part 20 is illustrated. The optical function part illustrated in FIG. 4 is one in which Au is vapor-deposited as a conductor layer so as to have a thickness of 50 nm on a fine structure part made of a nanoimprint resin having a plurality of pillars (each having a diameter of 120 nm and a height of 180 nm) periodically arranged at a predetermined pitch (a distance of 360 nm between center lines).

As illustrated in FIGS. 1, 2, and 3, the holding part 4 has a plurality of pinching parts 41 arranged around the optical function part 20 when seen in the thickness direction of the substrate 21 and leg parts 42 extending from the respective pinching parts 41 toward a rear face 3*b* of the transportation board 3. Fitting holes 11 are formed in the front face 3*a* of the transportation board 3 so as to correspond to the leg parts 42, respectively. The leg parts 42 are fitted into their corresponding fitting holes 11 in a state where the pinching parts 41 are in contact with the conductor layer 23 of the SERS element 2. The fitting holes 11 do not penetrate through the transportation board 3 but are bottomed. For example, the leg parts 42 and fitting holes 11 are formed cylindrical. The holding part 4 having the pinching parts 41 and leg parts 42 is integrally formed from materials such as resins (polypropylene, styrol resin, ABS resin, polyethylene, PET, PMMA, silicone, liquid crystal polymer, etc.), ceramics, glass, and silicon by using techniques such as molding, cutting, and etching.

Thus, the holding part 4 formed separately from the transportation board 3 is mechanically secured to the transportation board 3, while the SERS element 2 arranged in the depression 9 is pinched between the transportation board 3 and the pinching parts 41 of the holding part 4. By "mechanically" is meant herein "through fitting between members without adhesives and the like."

Figure 5:
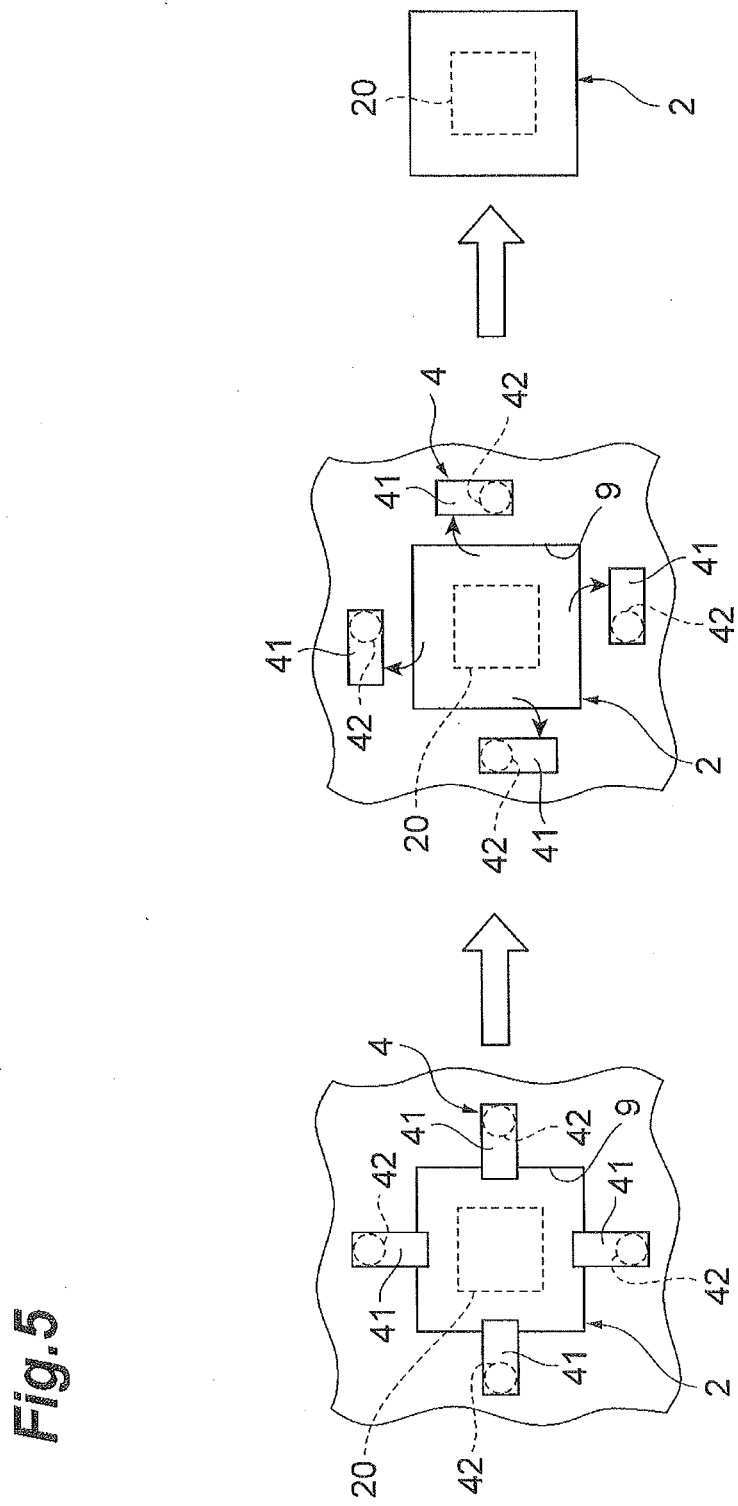
FIG. 5 is a diagram illustrating a procedure of Raman spectroscopic analysis using the surface-enhanced Raman scattering unit of FIG. 1.

A Raman spectroscopic analysis method using the SERS unit 1A will now be explained. First, as illustrated in FIG. 5, the SERS unit 1A is prepared, and the SERS element 2 is removed from the transportation board 3 (first step). More specifically, the pinching parts 41 are rotated around their corresponding leg parts 42 with respect to the transportation board 3, so as to be retracted from above the SERS element 2, whereby the SERS element 2 is taken out of the depression 9 of the transportation board 3. The holding part 4 may be removed from the transportation board 3, so as to take the SERS element 2 out of the depression 9 of the transportation board 3.

Figure 6:
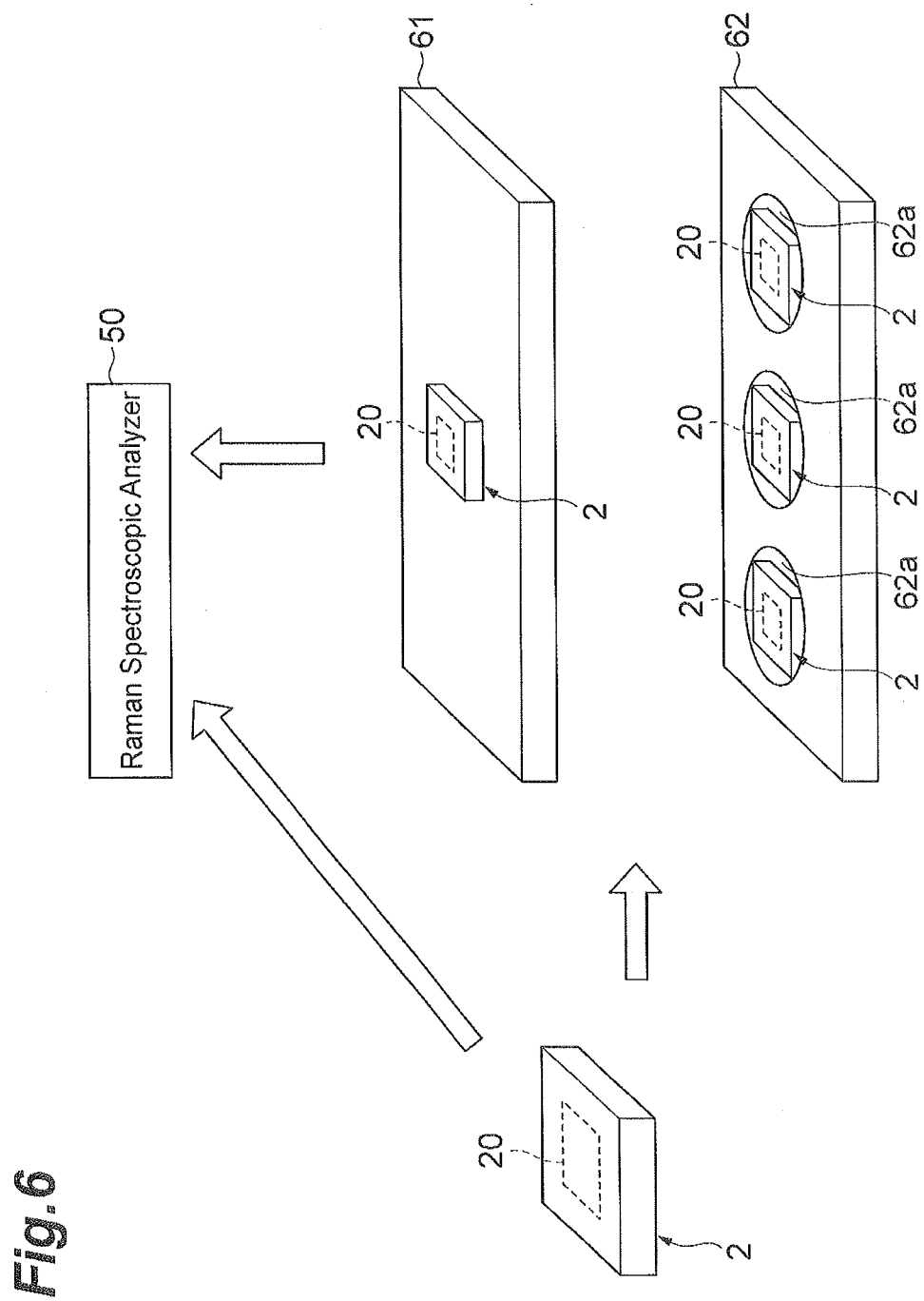
FIG. 6 is a diagram illustrating the procedure of Raman spectroscopic analysis using the surface-enhanced Raman scattering unit of FIG. 1.

Then, as illustrated in FIG. 6, a sample is arranged on the optical function part 20 of the SERS element 2 (second step). More specifically, the sample is arranged on the optical function part 20 in the SERS element 20 in a state where the SERS element 2 is placed on a glass slide 61, put into each of a plurality of depressions 62*a* in a support board 62, or left as it is.

Figure 7:
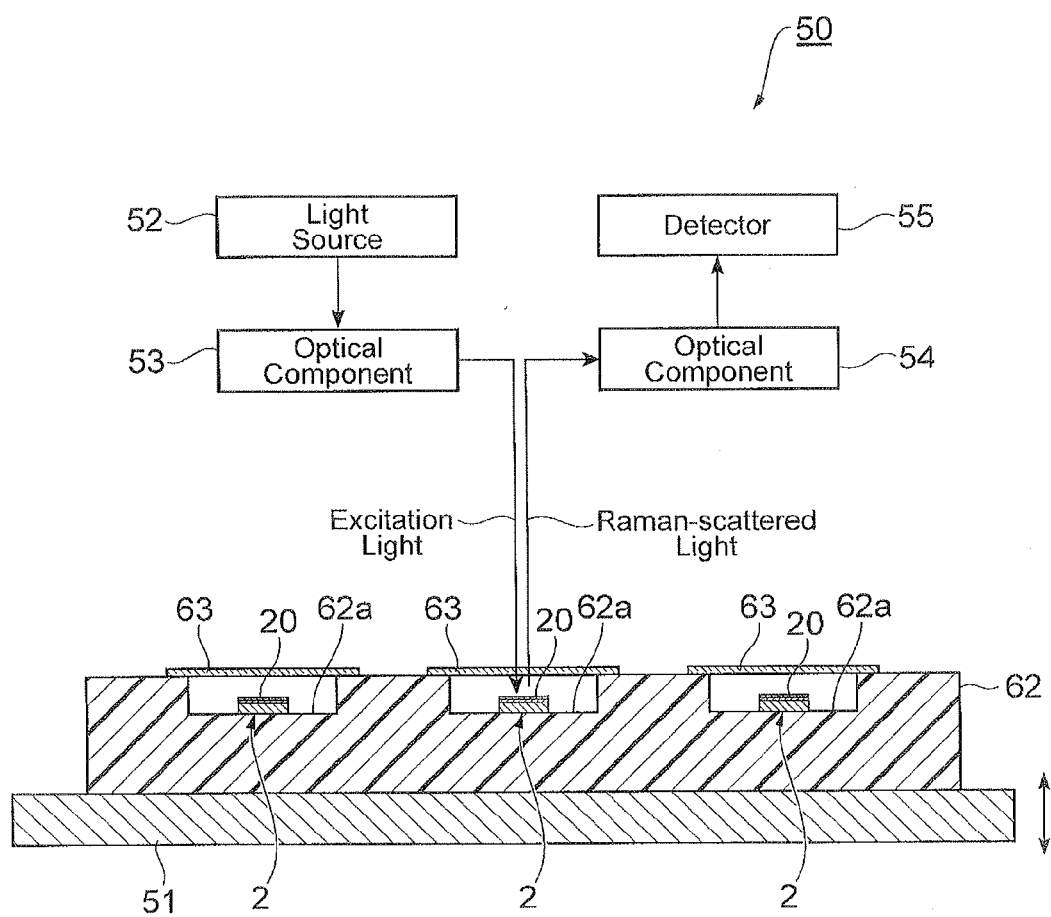
FIG. 7 is a structural diagram of a Raman spectroscopic analyzer to which the surface-enhanced Raman scattering unit of FIG. 1 is set.

Thereafter, the SERS element 2 in the above-mentioned state is set to a Raman spectroscopic analyzer 50, the sample arranged on the optical function part 20 is irradiated with excitation light, and Raman-scattered light derived from the sample is detected, so as to perform Raman spectroscopic analysis (third step). A case where the Raman spectroscopic analysis is performed in the Raman spectroscopic analyzer 50 comprising, as illustrated in FIG. 7, a stage 51 supporting the SERS element 2, a light source 52 for emitting excitation light, an optical component 53 for effecting collimation, filtering, condensing, and the like necessary for irradiating the optical function part 20 with the excitation light, an optical component 54 for effecting collimation, filtering, and the like necessary for guiding Raman-scattered light to a detector 55, and the detector 55 for detecting the Raman-scattered light will be explained in more detail here.

For example, a solution sample (or a dispersion of a powder sample in water or in a solution of ethanol) is put in the depressions 62*a* of the support board 62 on which the SERS element 2 is arranged, while cover slips 63 are brought into close contact with the solution sample in order to reduce the lens effect and the evaporation of the solution sample. In this state, the solution sample arranged on the optical function part 20 is irradiated with the excitation light emitted from the light source 52 through the optical component 53. At this time, the stage 51 is moved such that a focal point of the excitation light is located at the optical function part 20. This causes surface-enhanced Raman scattering at the interface between the optical function part 20 and the solution sample, whereby Raman-scattered light derived from the solution sample is released after being enhanced by about $10^8$ times, for example. The released Raman-scattered light is detected by the detector 55 through the optical component 54, so as to perform Raman spectroscopic analysis.

Not only the above-mentioned method but the following methods may also be used for arranging the sample on the optical function part 20. For example, the SERS element 2 may be held, so as to be dipped into a solution sample (or a dispersion of a powder sample in water or in a solution of ethanol or the like), lifted up, and then blown to dry. A minute amount of a solution sample (or a dispersion of a powder sample in water or in a solution of ethanol or the like) may be dropped on the optical function part 20 and left to dry. A powder sample may be dispersed as it is on the optical function part 20.

Effects exhibited by the SERS unit 1A will now be explained. First, the holding part 4 detachably holds the SERS element 2 in the transportation board 3 in the holding part 1A. Consequently, as compared with the case where the SERS element 2 is transported while sticking to a gel pack, a tape, or the like, for example, the optical function part 20 is inhibited from deteriorating because of components contained in the gel pack, ingredients of the sticking part of the tape, or the like. In addition, the SERS element 2 is pinched between the transportation board 3 and pinching parts 41. This makes it possible to hold the SERS element 2 securely in the transportation board 3. Therefore, the SERS unit 1A can inhibit the SERS element 2 from being damaged and the optical function part 20 from deteriorating during transportation. As a result, the Raman spectroscopic analysis method using the SERS unit 1A can accurately perform the Raman spectroscopic analysis.

Since the SERS element 2 is pinched between the transportation board 3 and pinching parts 41, the SERS unit 1A can prevent the molded layer 22 and conductor layer 23 formed on the substrate 21 in the SERS element 2 from peeling from the substrate 21 during transportation.

In the SERS unit 1A, the holding part 4 is formed separately from the transportation board 3 and mechanically secured to the transportation board 3. This can simplify the structure of the transportation board 3. In addition, as compared with the case where the holding part 4 is secured to the transportation board 3 with a tackifier or adhesive, for example, the optical function part 20 can be inhibited from deteriorating because of ingredients contained in the tackifier or adhesive.

In the SERS unit 1A, a plurality of pinching parts 41 are arranged around the optical function part 20. This makes it possible to hold the SERS element 2 stably in the transportation board 3.

In the SERS unit 1A, the transportation board 3 is provided with the depression 9 containing a part of the SERS element 2 on the substrate 21 side and restraining the SERS element 2 from moving in directions perpendicular to the thickness direction of the substrate 21. This can position the SERS element 2 with respect to the transportation board 3. This can also more securely prevent the SERS element 2 from shifting from the transportation board 3 and being damaged during transportation.

In the SERS unit 1A, the transportation board 3 is formed integrally from a resin. This configuration makes it harder for chipping to occur and thus can more securely inhibit the optical function part 20 from deteriorating because of chipped pieces adhering thereto.

Modified examples of the SERS unit 1A will now be explained. As illustrated in FIG. 8(*a*), guide grooves 15 for arranging the respective leg parts 42 of the holding part 4 may be provided in side faces of the depression 9 formed in the transportation board 3. This configuration enables the leg parts 42 to fit into the fitting holes 11 easily and securely. In this case, the leg parts 42 can also position the SERS element 2. As illustrated in FIG. 8(*b*), the depression 9 can also position the SERS element 2 in the case where the guide grooves 15 are provided.

Figure 9:
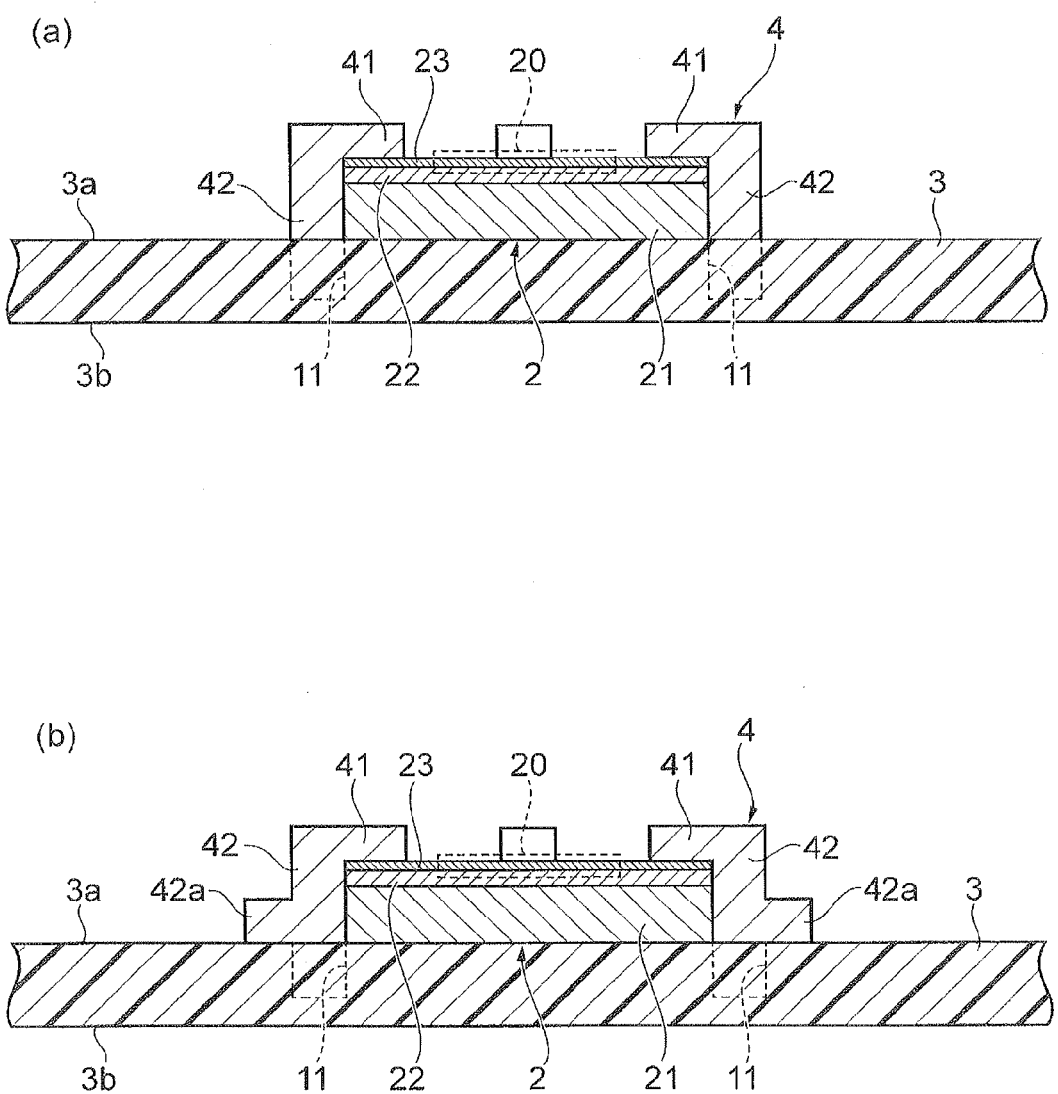
FIG. 9 is a partly enlarged sectional view of modified examples of the surface-enhanced Raman scattering unit of FIG. 1.

As illustrated in FIG. 9(*a*), the SERS element 2 may be arranged on the front face 3*a* of the transportation board 3. That is, the lower face of the substrate 21 of the SERS element 2 may abut against the front face 3*a* of the measurement board 3. This configuration can improve the strength of the transportation board 3 by the absence of the depression 9. As illustrated in FIG. 9(*b*), the leg parts 42 of the holding part 4 may be formed with stoppers 42*a*, respectively. In this configuration, fitting the leg parts 42 into the fitting holes 11 until the stoppers 42*a* come into contact with the transportation board 3 enables the pinching parts 41 to come into contact with the SERS element 2 and exert a substantially fixed pressure thereon, thereby preventing the pressure from acting more than necessary on the SERS element 2.

As illustrated in FIG. 10, for restricting rotation areas of the pinching parts 41 when the pinching parts 41 are rotated around the leg parts 42 with respect to the transportation board 3, the front face 3*a* of the transportation board 3 may be provided with depressions 16. At a stage prior to assembling the SERS unit 1A, this configuration enables the pinching parts 41 to be retracted from above the depression 9 of the transportation board 3 to substantially fixed positions. Therefore, when assembling the SERS unit 1A, an operation of rotating the pinching parts 41 around the leg parts 42 so as to make the holding part 4 hold the SERS element 2 can be done efficiently.

Figure 12:
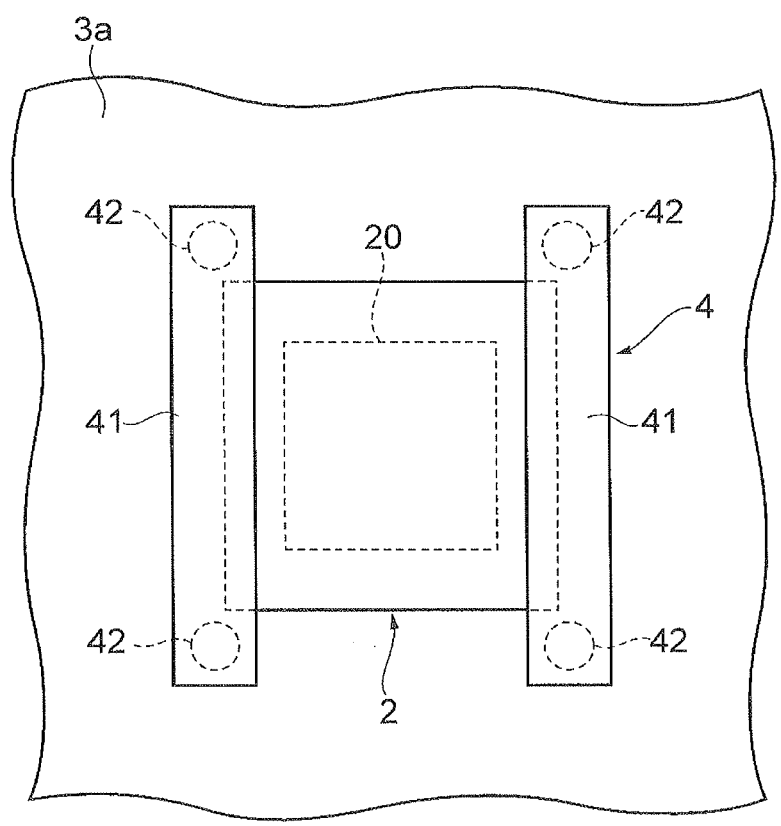
FIG. 12 is a partly enlarged plan view of a modified example of the surface-enhanced Raman scattering unit of FIG. 1.

As illustrated in FIG. 11, the holding part 4 may engage the transportation board 3 such that the holding parts 41 can advance and retract with respect to the SERS element 2 arranged in the depression 9. As illustrated in FIG. 12, a plurality of pinching parts 41 may be arranged such as to come into contact with the SERS element 2 in each of areas opposing each other in the ring-shaped region in the outer edge of the SERS element 2.

Second Embodiment

Figure 13:
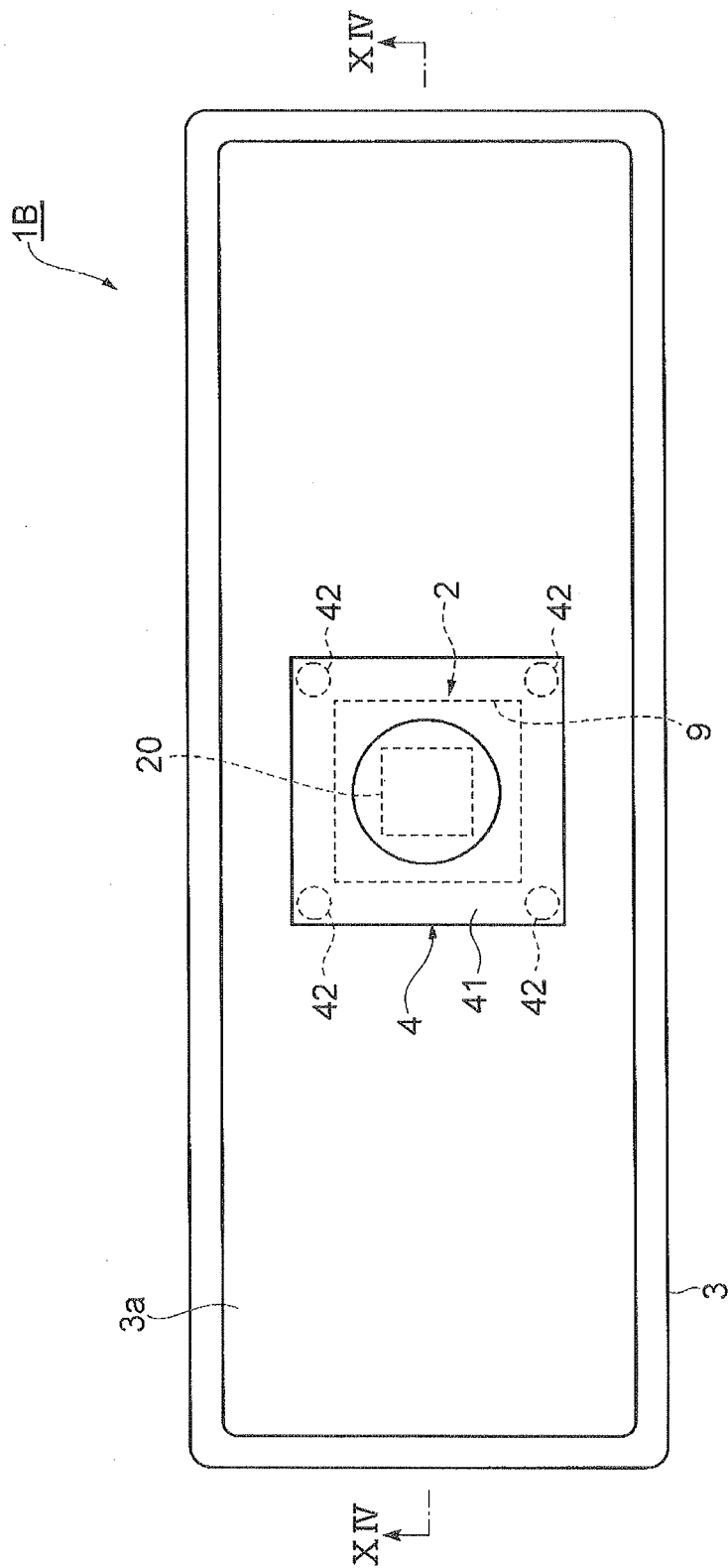
FIG. 13 is a plan view of the surface-enhanced Raman scattering unit in accordance with a second embodiment of the present invention.
Figure 14:
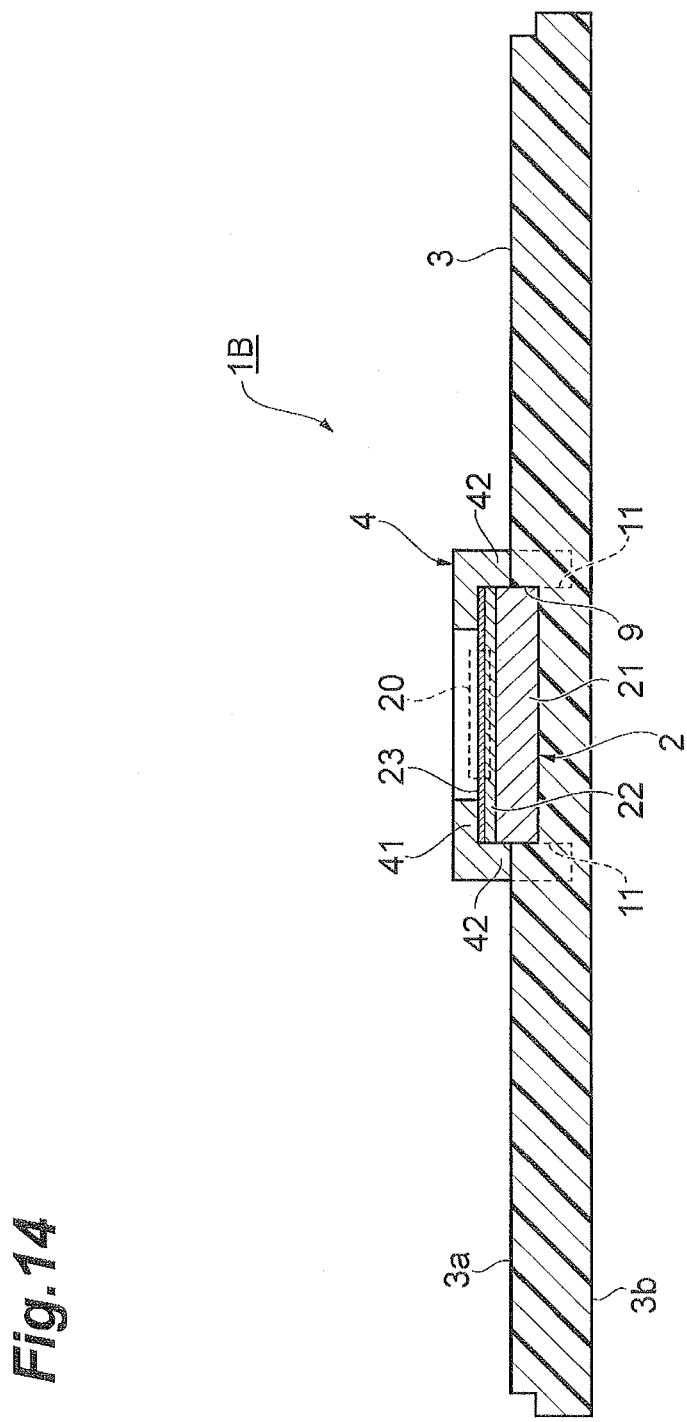
FIG. 14 is a sectional view of the surface-enhanced Raman scattering unit taken along the line XIV-XIV of FIG. 13.

As illustrated in FIGS. 13 and 14, a SERS unit 1B differs from the above-mentioned SERS unit 1A mainly in that the pinching part 41 is formed into a ring so as to surround the optical function part 20 when seen in the thickness direction of the substrate 21. In the SERS unit 1B, the holding part 4 has the pinching part 41 formed into a ring so as to surround the optical function part 20 when seen in the thickness direction of the substrate 21 and a plurality of leg parts 42 extending from the pinching part 41 toward the rear face 3*b* of the transportation board 3. Fitting holes 11 are formed in the front face 3*a* of the transportation board 3 so as to correspond to the leg parts 42, respectively. The leg parts 42 are fitted into their corresponding fitting holes 11 in a state where the pinching part 41 surrounds the optical function part 20 and is in contact with the conductor layer 23 of the SERS element 2. Thus, the holding part 4 formed separately from the transportation board 3 is mechanically secured to the transportation board 3, while the SERS element 2 arranged in the depression 9 is held between the transportation board 3 and the pinching part 41 of the holding part 4.

For example, the pinching part 41 is formed such as to have a rectangular outer edge and a circular inner edge when seen in the thickness direction of the substrate 21, while the leg parts 42 extend from four corners of the pinching part 41, respectively, toward the rear face 3*b* of the transportation board 3. Making the inner edge of the pinching part 41 circular prevents pressures from acting locally on the SERS element 2. The leg parts 42 and fitting holes 11 are formed cylindrical. The holding part 4 having the pinching part 41 and leg parts 42 is integrally formed from materials such as resins (polypropylene, styrol resin, ABS resin, polyethylene, PET, PMMA, silicone, liquid crystal polymer, etc.), ceramics, glass, and silicon by using techniques such as molding, cutting, and etching.

The SERS unit 1B constructed as in the foregoing can inhibit the SERS element 2 from being damaged and deteriorating during transportation as with the above-mentioned SERS unit 1A. Upon measurement, the SERS element 2 can be taken out of the transportation board 3 by removing the holding part 4 from the transportation board 3.

In the SERS unit 1B, the pinching part 41 is formed into a ring so as to surround the optical function part 20 when seen in the thickness direction of the substrate 21. This can hold the SERS element 2 stably in the transportation board 3.

Modified examples of the SERS unit 1B will now be explained. As illustrated in FIG. 15, the pinching part 41 of the holding part 4 may be formed such as to have a rectangular inner edge when seen in the thickness direction of the substrate 21. As illustrated in FIG. 15(*a*), the pinching part 41 may be formed such as to come into contact with the SERS element 2 in the ring-shaped region in its inner edge. As illustrated in FIG. 15(*b*), the pinching part 41 may be formed such as to come into contact with the SERS element 2 in areas opposing each other in the ring-shaped region in its inner edge. As illustrated in FIG. 15(*c*), the pinching part 41 may be formed such as to come into contact with the SERS element 2 at a plurality of projections 41*b* formed in its inner edge.

As illustrated in FIG. 16, one of parts opposing each other in the ring-shaped pinching part 41 may be rotatably supported by the transportation board 3, while the other is adapted to engage the transportation board 3. This configuration makes it possible to manage the transportation board 3 and holding part 4 in a state where the holding part 4 is attached to the transportation board 3. When assembling the SERS unit 1B, arranging the SERS element 2 in the depression 9 in a state where the holding part 4 is open and then closing the holding part 4 and making the other part of the pinching part 41 engage the transportation board 3 enables the holding part 4 to hold the SERS element 2 easily. Upon measurement, the SERS element 2 can be removed from the transportation board 3 in a procedure reversed from that of assembling the SERS unit 1B. For making it easier to open and close the holding part 4, a spring may be installed between the one part of the holding part 4 and the transportation board 3.

Figure 17:
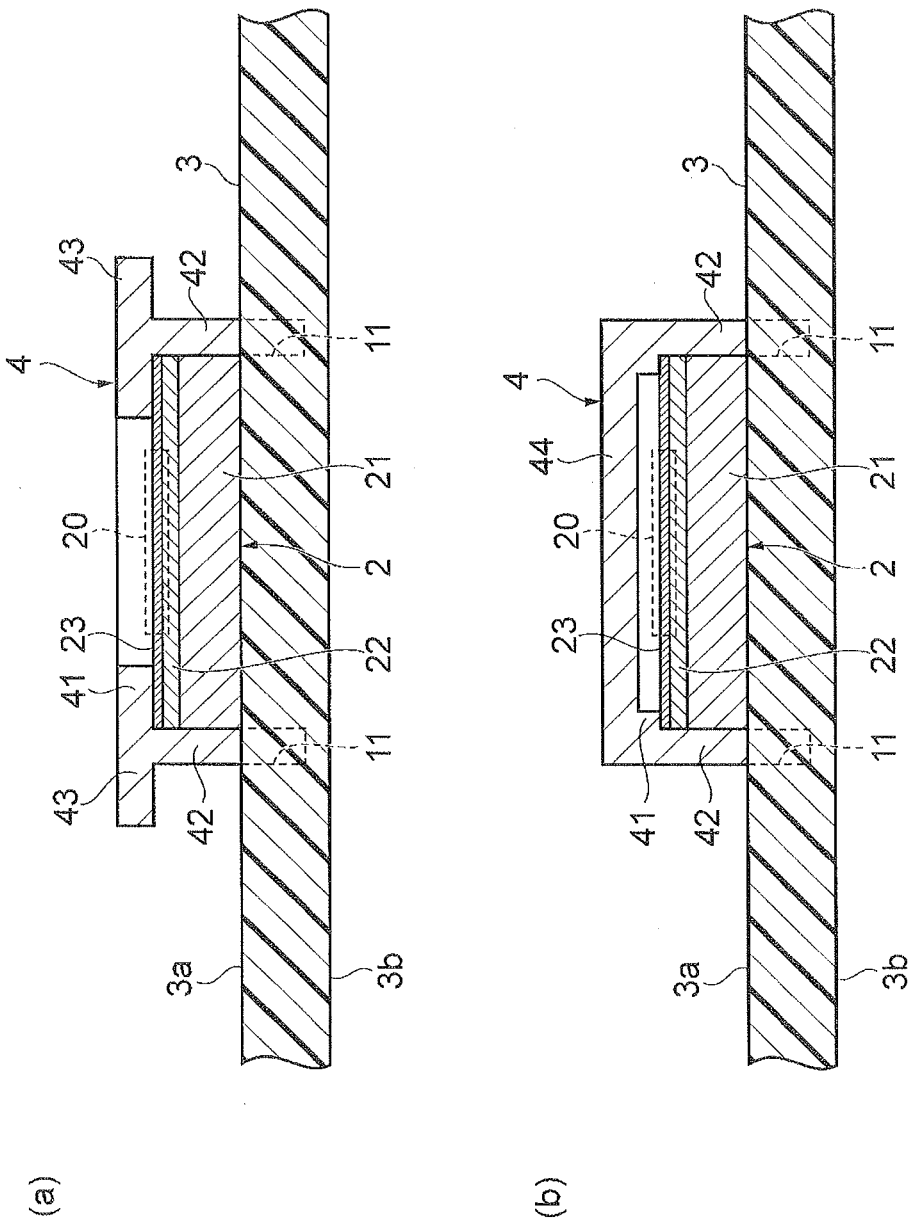
FIG. 17 is a partly enlarged sectional view of modified examples of the surface-enhanced Raman scattering unit of FIG. 13.

As illustrated in FIG. 17(*a*), the holding part 4 may have a projection 43 projecting outward from the pinching part 41 or leg part 42 while forming a gap between the holding part 4 and the front face 3*a* of the transportation board 3. This configuration makes it easy to remove the holding part 4 from the transportation board 3 by catching the projection 43 with a jig or the like. As illustrated in FIG. 17(*b*), the holding part 4 may have a cover 44 for covering the opening of the pinching part 41 formed into a ring. This configuration can prevent the optical function part 20 from being damaged and so forth because of some members coming into contact with the optical function part 20 during transportation. The projection 43 may be formed either integrally with or separately from the pinching part 41 or leg part 42. Similarly, the cover 44 may be formed either integrally with or separately from the pinching part 41.

Third Embodiment

As illustrated in FIG. 18, a SERS unit 1C differs from the above-mentioned SERS unit 1A mainly in that the holding part 4 is integrally formed with the transportation board 3. When assembling the SERS unit 1C, the holding part 4 is deformed so as to open each pinching part 41 as illustrated in FIG. 18(*a*), whereby the SERS element 2 is arranged in the transportation board 3, and then the deformed holding part 4 is returned to its original state so as to close each pinching part 41 as illustrated in FIG. 18(*b*), thereby making the holding part 4 hold the SERS element 2.

The SERS unit 1C constructed as in the foregoing can inhibit the SERS element 2 from being damaged and the optical function part 20 from deteriorating during transportation as with the above-mentioned SERS unit 1A. Upon measurement, the SERS element 2 can be removed from the transportation board 3 in a procedure reversed from that of assembling the SERS unit 1C.

In the SERS unit 1C, the holding part 4 is formed integrally with the transportation board 3. This can reduce the number of components in the SERS unit 1C. In addition, as compared with the case where the holding part 4 is secured to the transportation board 3 with a tackifier or adhesive, for example, the optical function part 20 can be inhibited from deteriorating because of ingredients contained in the tackifier or adhesive.

Figure 19:
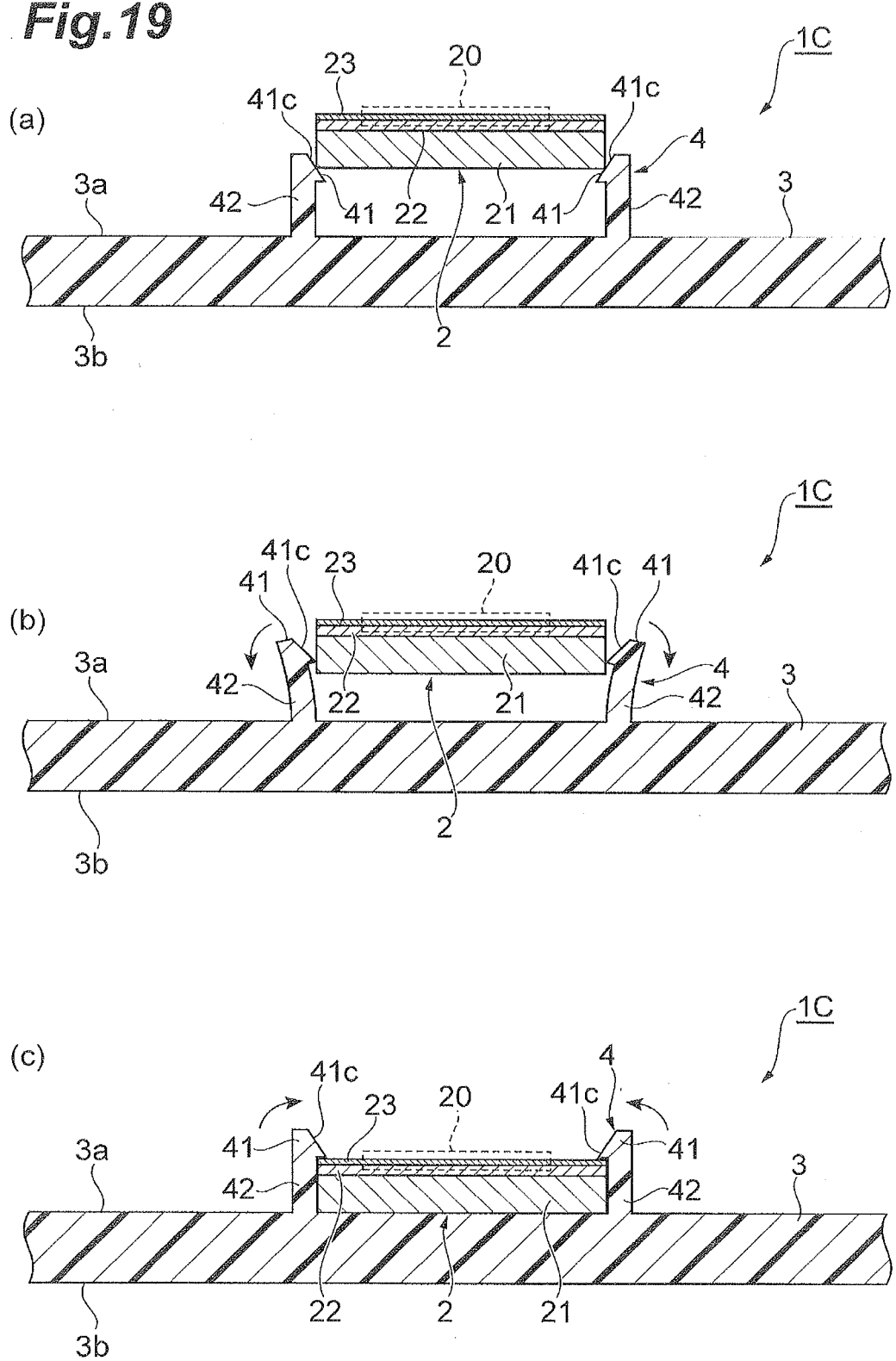
FIG. 19 is a partly enlarged sectional view of a modified example of the surface-enhanced Raman scattering unit of FIG. 18.

Modified examples of the SERS unit 1C will now be explained. As illustrated in FIG. 19, each pinching part 41 may have a tilted surface 41 formed so as to widen toward the side opposite from the transportation board 3. This configuration can easily guide the SERS element 2 to its holding position in the transportation board 3 when assembling the SERS unit 1C. As illustrated in FIG. 20, each pinching part 41 may have a tilted surface 41*d* formed so as to widen toward the transportation board 3. This configuration can facilitate an operation of deforming the holding part 4 so as to open each pinching part 41 when assembling the SERS unit 1C and when removing the SERS element 2 from the transportation board 3 upon measurement. As illustrated in FIG. 21, each pinching part 41 may have a cutout 41*e* for engaging a jig 60 used for the operation of deforming the holding part 4 so as to open each pinching part 41. This configuration can facilitate the operation of deforming the holding part 4 so as to open each pinching part 41 by using the jig 60, while securely preventing the jig 60 from coming into contact with the optical function part 20 when assembling the SERS unit 1C and when removing the SERS element 2 from the transportation board 3 upon measurement.

While the first to third embodiments of the present invention are explained in the foregoing, the present invention is not limited to the above-mentioned embodiments. For example, as illustrated in FIG. 22, a plurality of SERS elements 2 may be arranged on the transportation board 3 and detachably held by the holding part 4 in a SERS unit 1D.

As illustrated in FIG. 22(a), the holding part 4 may be integrally formed with all the SERS elements 2. This configuration makes it possible to remove all the SERS elements 2 collectively from the transportation board 3. The holding part 4 may be divided into groups of a plurality of SERS elements 2 as illustrated in FIG. 22(b) or into the respective SERS elements 2 as illustrated in FIG. 22(c). These configurations make it possible to remove a specific number of SERS elements 2 or one SERS element 2 from the transportation board 3.

As illustrated in FIG. 23, when a plurality of SERS elements 2 are arranged on the transportation board 3 and detachably held by the holding part 4 in the SERS unit 1D, the transportation board 3 and holding part 4 may be constructed so as to be dividable. At this time, as illustrated in FIG. 23(a), the transportation board 3 integrally formed for all the SERS elements 2 may be provided with grooves 17 for dividing the transportation board 3 into the respective SERS elements 2 (or into groups of a plurality of SERS elements 2), while a plurality of holding parts 4 are formed for the respective SERS elements 2 (or for the respective groups of a plurality of SERS elements 2). As illustrated in FIG. 23(b), the holding part 4 integrally formed for all the SERS elements 2 may be provided with grooves 18 for dividing the holding part 4 into the respective SERS elements 2 (or into groups of a plurality of SERS elements 2), while a plurality of transportation boards 3 are formed for the respective SERS elements 2 (or for the respective groups of a plurality of SERS elements 2). As illustrated in FIG. 23(c), the transportation board 3 integrally formed for all the SERS elements 2 may be provided with grooves 17 for dividing the transportation board 3 into the respective SERS elements 2 (or into groups of a plurality of SERS elements 2), while the holding part 4 integrally formed for all the SERS elements 2 is provided with grooves 18 for dividing the holding part 4 into the respective SERS elements 2 (or into groups of a plurality of SERS elements 2). By dividing the transportation board 3 and holding part 4 along the grooves 17, 18, these configurations make it possible to yield the SERS element 2 in a state pinched between the transportation board 3 and holding part 4.

The material for the transportation board 3 is not limited to resins, but may be low-melting glass, ceramics, and the like. The transportation board 3 can be formed by integral molding from low-melting glass as from a resin. From a ceramic, the transportation board 3 can be formed by firing. Various materials and forms in addition to those mentioned above can be employed for the structures of the SERS units 1A to 1D. The ring shape is not limited to circular rings, but encompasses other ring shapes such as rectangular rings.

The fine structure part 24 may be formed on the front face 21a of the substrate 21 either indirectly with the support part 25, for example, interposed therebetween or directly. The conductor layer 23 is not limited to the one directly formed on the fine structure part 24, but may indirectly be formed on the fine structure part 24 through some layers such as layers of buffer metals (Ti, Cr, and the like) for improving the adhesion of the metal to the fine structure part 24.

INDUSTRIAL APPLICABILITY

The present invention can provide a surface-enhanced Raman scattering unit which can inhibit the surface-enhanced Raman scattering element from being damaged and the optical function part from deteriorating during transportation and a Raman spectroscopic analysis method using such a surface-enhanced Raman scattering unit.

REFERENCE SIGNS LIST 1A, 1B, 1C, 1D: SERS unit (surface-enhanced Raman scattering unit);
2: SERS element (surface-enhanced Raman scattering element);
3: transportation board;
4: holding part;
9: depression;
20: optical function part;
21: substrate;
41: pinching part.

The invention claimed is:

1. A surface-enhanced Raman scattering unit having a front face, a rear face, and a thickness direction that is orthogonal to the front face and rear face, comprising:
a surface-enhanced Raman scattering element having a substrate and an optical scattering surface for generating surface-enhanced Raman scattering, the optical surface being formed on the substrate;
a transportation board supporting the surface-enhanced Raman scattering element during transportation, the surface-enhanced Raman scattering element being removed from the transportation board upon measurement; and
a pinching part of a holding part surrounding the optical scattering surface in the thickness direction, the pinching part having legs extending from the pinching part and pinching the surface-enhanced Raman scattering element in cooperation with the transportation board, and detachably holding the surface-enhanced Raman scattering element in the transportation board.

2. A surface-enhanced Raman scattering unit according to claim 1, wherein the holding part is formed separately from the transportation board and mechanically secured to the transportation board.

3. A surface-enhanced Raman scattering unit according to claim 1, wherein the holding part is formed integrally with the transportation board.

4. A surface-enhanced Raman scattering unit according to claim 1, wherein the pinching part is formed into a ring.

5. A surface-enhanced Raman scattering unit according to claim 1, wherein a plurality of such pinching parts are arranged around the optical scattering surface.

6. A surface-enhanced Raman scattering unit according to claim 1, wherein the transportation board is provided with a depression containing at least a part of the surface-enhanced Raman scattering element on the substrate side and restraining the surface-enhanced Raman scattering element from moving in a direction perpendicular to the thickness direction of the substrate.

7. A surface-enhanced Raman scattering unit according to claim 1, wherein the transportation board is formed integrally from a resin.

8. A Raman spectroscopic analysis method comprising:
a first step of preparing the surface-enhanced Raman scattering unit according to claim 1 and removing the surface-enhanced Raman scattering element from the transportation board;
a second step, after the first step, of arranging a sample on the optical scattering surface of the surface-enhanced Raman scattering element; and
a third step, after the second step, of setting the surface-enhanced Raman scattering unit to a Raman spectroscopic analyzer, irradiating the sample arranged on the optical scattering surface with excitation light, and detecting Raman-scattered light derived from the sample, so as to perform Raman spectroscopic analysis.

9. A surface-enhanced Raman scattering unit comprising:
a surface-enhanced Raman scattering element having a substrate and an optical scattering surface formed on the substrate, the optical scattering surface being configured to generate surface-enhanced Raman scattering;
a transportation board supporting the surface-enhanced Raman scattering element during transportation, the surface-enhanced Raman scattering element being removed from the transportation board upon measurement; and
a holding part having a projection configured to extend over the surface-enhanced Raman scattering element, in order to detachably hold the surface-enhanced Raman scattering element against the transportation board.

10. A surface-enhanced Raman scattering unit according to claim 9, wherein the holding part is formed separately from the transportation board and mechanically secured to the transportation board.

11. A surface-enhanced Raman scattering unit according to claim 9, wherein the holding part is formed integrally with the transportation board.

12. A surface-enhanced Raman scattering unit according to claim 9, wherein the projection is formed into a ring so as to surround the optical scattering surface when seen in a thickness direction of the substrate.

13. A surface-enhanced Raman scattering unit according to claim 9, wherein a plurality of such projections are arranged around the optical scattering surface.

14. A surface-enhanced Raman scattering unit according to claim 9, wherein the transportation board is provided with a depression containing at least a part of the surface-enhanced Raman scattering element on the substrate side and restraining the surface-enhanced Raman scattering element from moving in a direction perpendicular to a thickness direction of the substrate.

15. A surface-enhanced Raman scattering unit according to claim 9, wherein the transportation board is formed integrally from a resin.

16. The surface-enhanced Raman scattering unit according to claim 9, wherein the holding part further comprises a leg formed integrally with the projection.

17. The surface-enhanced Raman scattering unit according to claim 16, wherein the transportation board comprises fitting holes for receiving the leg.

18. A Raman spectroscopic analysis method comprising:
a first step of preparing the surface-enhanced Raman scattering unit according to claim 9 and removing the surface-enhanced Raman scattering element from the transportation board;
a second step, after the first step, of arranging a sample on the optical scattering surface of the surface-enhanced Raman scattering element; and
a third step, after the second step, of setting the surface-enhanced Raman scattering unit to a Raman spectroscopic analyzer, irradiating the sample arranged on the optical scattering surface with excitation light, and detecting Raman-scattered light derived from the sample, so as to perform Raman spectroscopic analysis.

* * * * *